(12) United States Patent
Parkin et al.

(10) Patent No.: US 7,384,734 B2
(45) Date of Patent: Jun. 10, 2008

(54) COMPOSITIONS AND METHODS FOR DETERMINING THE SUSCEPTIBILITY OF A PATHOGENIC VIRUS TO PROTEASE INHIBITORS

(75) Inventors: Neil T. Parkin, Belmont, CA (US); Colombe Chappey, San Francisco, CA (US); Christos J. Petropoulos, South San Francisco, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 663 days.

(21) Appl. No.: 10/367,223

(22) Filed: Feb. 13, 2003

(65) Prior Publication Data

US 2004/0224307 A1 Nov. 11, 2004

Related U.S. Application Data

(60) Provisional application No. 60/357,171, filed on Feb. 15, 2002, provisional application No. 60/359,342, filed on Feb. 22, 2002, provisional application No. 60/392,377, filed on Jun. 26, 2002.

(51) Int. Cl.
*C12Q 1/70* (2006.01)
(52) U.S. Cl. .......................... 435/5; 424/188.1
(58) Field of Classification Search .............. 435/5; 424/188.1, 208.1
See application file for complete search history.

(56) References Cited

U.S. PATENT DOCUMENTS

| | | | |
|---|---|---|---|
| 5,436,131 | A | 7/1995 | Condra et al. |
| 5,766,842 | A | 6/1998 | Melnick et al. |
| 5,837,464 | A | 11/1998 | Capon et al. |
| 6,033,902 | A | 3/2000 | Haseltine et al. |
| 6,103,462 | A | 8/2000 | Paulous et al. |
| 6,242,187 | B1 | 6/2001 | Capon et al. |
| 2002/0064838 | A1 | 5/2002 | Parkin et al. |
| 2003/0108857 | A1 | 6/2003 | Parkin et al. |
| 2004/0106106 | A1 | 6/2004 | Parkin et al. |

FOREIGN PATENT DOCUMENTS

| | | |
|---|---|---|
| WO | WO99/67427 | 6/1999 |
| WO | WO00/78996 | 12/2000 |
| WO | WO02/22076 | 3/2002 |
| WO | WO02/068618 | 9/2002 |
| WO | WO02/099387 | 12/2002 |
| WO | WO03/070700 | 8/2003 |
| WO | WO2004/003512 | 1/2004 |
| WO | WO2004/003514 | 1/2004 |

OTHER PUBLICATIONS

Lin, Y.-C., et al., 2003, "Structural basis for distinctions between substrate and inhibitor specifities for feline immunodeficiency virus and human immunodeficiency virus proteases", J. Virol. 77(12):6589-6600.*

Choudhury, S., et al., 2003, "Mutagenesis of the dimer interface residues of tethered and untethered HIV-1 protease result in differential activity and suggest multiple mechanisms of compensation", Virol. 307:204-212.*

Int'l Search Report for PCT/US00/17178, filed Dec. 2000, PCT.
Int'l Search Report for PCT/US01/28754, filed Mar. 2002, PCT.
Int'l Search Report for PCT/US02/01682, filed Sep. 2002, PCT.
Int'l Search Report for PCT/US02/18684, filed Jan. 2003, PCT.
Int'l Search Report for PCT/US03/04362, filed Dec. 2004, PCT.
Int'l Search Report for PCT/US03/21023, filed Jul. 2004, PCT.
Carrillo et al., (1998), "In Vitro Selection and Characterization of Human Immunodefciency Virus Type 1 Variants With Increased Resistance to ABT-378, a Novel Protease Inhibitor," *Journal of Virology*, 72(9): 7532-41.
Condra et al., (1996), "Genetic Correlates of In Vivo Resistance to Indinavir, a Human Immunodeficiency Virus Type 1 Protease Inhibitor ," *Journal of Virology*, 70(12): 8270-76.
Int'l Search Report for PCT/US03/21335, filed May 2004, PCT.
Craig et al., 1998 "HIV Protease Genotype and Viral Sensitivity to HIV Protease Inhibitors Following Saquinavir Therapy", *AIDS*, 12: 1611-1618.
Dreyer GB, et al."A Symmetric Inhibitor Binds HIV-1 Protease Asymmetrically" *Biochemistry* (1993) 32:937-947.
J. Eron, et al., (1995) Preliminary Assessment of 141 W94 in Combination with Other Protease Inhibitors, *5th Conference on Retroviruses and Opportunistic Infections*.
Genbank Accession No. P12497 POL Polyprotein (2004).
Genbank Accession No. AF324493 HIV-1 vector pNL4 . . . [gi:12831134] (2001).
Gervaix, et al., (1997), "A New Reporter Cell Line to Monitor HIV Infection and Drug Susceptibility in Vitro," *Proc. Natl. Acad. Sci. USA*, 94:4653-4658.
Gong et al., (2000), "In Vitro Resistance Profile of the Human Immunodeficiency Virus Type 1 Protease Inhibitor BMS-232632," *Antimicrobial Agents and Chemotherapy*, 44(9): 2319-26.
Gunthard, et al., (1998), "Comparative Performance of High-Density Oligonucleotide Sequencing and Dideoxynucleotide Sequencing of HIV Type 1 *pol* From Clinical Samples," *Aids Research and Human Retroviruses*. 14(10): 869-876.

(Continued)

*Primary Examiner*—Jeffrey S. Parkin
(74) *Attorney, Agent, or Firm*—Jones Day

(57) ABSTRACT

The present invention provides an approach for developing an algorithm for determining the effectiveness of anti-viral drugs based on a comprehensive analysis of paired phenotypic and genotypic data guided by phenotypic clinical cut-offs. In one aspect, the algorithm allows one to provide a patient with effective treatment. It helps predict whether an infected individual will respond to treatment with an anti-viral compound, thereby allowing an effective treatment regimen to be designed without subjecting the patient to unnecessary side effects. Also, by avoiding the administration of ineffective drugs, considerable time and money is saved.

19 Claims, 18 Drawing Sheets

OTHER PUBLICATIONS

Haubrich et al., (2001), "CCTG 575: A Randomized. Prospective Study of Phenotype Testing Versus Standard of Care For Patients Failing Antiretroviral Therapy," *Antiviral Therapy*, 6(Supplement 1): 63.

Hazuda, et al., 2000 "Inhibitors of Strand Transfer That Prevent Integration and Inhibit HIV-1 Replication in Cells," *Science* 287: 646-650.

Herrmann, et al., (1997), "A Working Hypotheses-Virus Resistance Development As An Indicator of Specific Antiviral Activity," *Ann. NY Acad Sciences*, 284: 632-637.

Hertogs, et al., (1998), "A Rapid Method for Simultaneous Detection of Phenotypic Resistance to Inhibitors of Protease and Reverse Transcriptase in Recombinant Human Immunodeficiency Virus Type 1 Isolates From Patients Treated with Antiretroviral Drugs," *Antimicrobial Agents and Chemotherapy*, 42(2): 269-276.

Hill, A. et al. (1998) "Low frequency of genotypic mutations associated with resistance to AZT and 3TC after combination treatment with indinavir," *Int. Conf. AIDS* 12:812, (Abstract No. 6).

Hirsch, et al., (2000), "Antiretroviral Drug Resistance Testing in Adult HIV-1 Infection" *JAMA*, 283(18): 2417-26.

Katzenstein et al., (2002), "Baseline Phenotypic Susceptibility and Virologic failure over 144 weeks Among Nucleoside RT Inhibitor Experienced Subjects in ACTG 364," Antiretroviral Drug Resistance Testing in Adult HIV-1 Infection, *2002 9th Conference on Retroviruses and Opportunistic Infections*, Session 77 Poster Session 591-T.

Katzenstein et al., (2002), "The Inhibitory Quotient (IQ) for Saquinavir (SQV) Predicts Virologic Response to Salvage Therapy" *2002 9th Conference on Retroviruses and Opportunistic Infections*, Session 28 Poster Session 129.

Kempf et al., (2001), "Identification of Genotypic Changes in Human Immunodeficiency Virus Protease that Correlate With Reduced Susceptibility to the Protease Inhibitor Lopinavir Among Viral Isolates From Protease Inhibitor-Experienced Patients," *Journal of Virology*, 75(16): 7462-69.

Kim, (1995) "Crystal Structure of HIV-1 Protease in Complex with VX-478, a Potent and Orally Bioavailable Inhibitor of the Enzyme," *J. Am. Chem. Soc.*, 117: 1181-1182.

Lambert DM, et al. (1992) "Human Immunodeficiency Virus Type 1 Protease Inhibitors Irreversibly Block Infectivity of Purified Virions From Chronically Infected Cells" *Anit Microb Agents Chem* 36:982-98.

Larder, et al., (1995) "Potential Mechanism for; Sustained Antiretroviral Efficacy of AZT-3TC Combination Therapy," *Science*, 269, 696-699.

Lazdins, et al., (1997) "In Vitro Effect of al-Acid Glycoprotein on the Anti-Human Immunodeficiency Virus (HIV) Activity of the Inhibitor CGP 61775: A Comparative Study wits Other Relevant HIV Protease Inhibitors," *J Infec. Dis.*, 175: 1063-1070.

Livingston, (1995) "Weak Binding of VX-478 tc Human Plasma Proteins and Implications for Anti-Humar Immunodeficiency Virus Therapy," *J Infec. Dis.*, 172:1.238-124.

Maguire et al., (2002), "Emergence of Resistance to Protease Inhibitor Amprenavir in Human Immunodeficiency Virus Type 1-Infected Patients: Selection of Four Alternative Viral Protease Genotypes and Influence of Viral Susceptibility to Coadministered Reverse Transcriptase Nucleoside Inhibitors," *Antimicrobial Agents and Chemotherapy*, 46(3): 731-738.

Mahalingam, et al., (1999) "Structural and Kinetic Analysis of Drug Resistant Mutants of HIV Protease," *Biochem.*, 263: 1-9.

Miller M, et al. (1989) Structure of Complex of Synthetic HIV-lj Protease with a SubstrateBased Inhibitor at 2.3 A Resolution, *Science* 246:1149-1152.

Mohri H, et al. (1993) "Quantitation of Zidovudine-Resistant Human Immunodeficiency Virus Type 1 in the Blood of Treated and Untreated Patients," *PNAS* 90:25-29.

Murphy, et al., (1999) "Treatment with Amprenavir Alone or Amprenavir with Zidovudine and Lamivudine in Adults with Human Immunodeficiency Virus Infection" *J. Infec. Dis.*, 179: 808-81 E.

Najera I, et al. (1994) "Natural Occurrence of Drug ResistancE Mutations in the Reverse Transcriptase of Human Immunodeficiency Virus Type 1 Isolates," *Aids Res Hum Retroviruses* 10:1479-1488.

Najera I, et al. (1995) "pol Gene Quasispecies of Humar Immunodeficiency Virus: Mutations Associated with Drug ResistancE Virus From Patients Undergoing No Drug Therapy," *J Virol* 69:23-31.

Palmer, et al., (1999) "Highly Drug-resistant HIV-1 Clinical Isolates Are Cross-resistant to Many Antiretroviral Compounds in Current Clinical Development," *AIDS*, 13: 661-667.

Parkin, et al., (1999) "Phenotypic changes in Drug Susceptibility Associated with Failure of Human Immunodeficiency Virus Type 1 (HIV-1) Triple Combination Therapy," *J Infec. Dis.*, 180: 865-870.

Partaledis, et al., (1995) "In Vitro Selection and Characterization of Human Immunodeficiency Virus Type 1 (HIV-1) Isolates with Reduced Sensitivity to Hydroxyethylamino Sulfonamide Inhibitors of HIV-1 Aspartyl Protease," *Journal of Virology*, 69: 5228-5235.

Patick, et al., (1998) "Genotypic and Phenotypic Characterization of Human Immunodeficiency Virus Type 1 Variants Isolated from Patients Treated with the Protease Inhibitor Nelfinavir," *Antimicrobial Agents and Chemotherapy*, 42(10): 2637-44.

Petit SC, et al. (1993) "The Specificity of the HIV-1 Protease" *Drug Discov Des* 1:69-83.

Petropoulos, et al., (2000), "A Novel Phenotypic Drug Susceptibility Assay For Human Immunodeficiency Virus Type 1," *Antimicrobial Agents and Chemotherapy*, 44(4): 920-928.

Race, et al., (1999), "Analysis of HIV Cross-Resistance to Protease Inhibitors Using A Rapid Single-Cycle Recombinant Virus Assay For Patients Failing On Combination Therapies," *AIDS*, 13(15): 2061-2068.

Roberts NA, et al. (1990) "Rational Design of Peptide-Based HIV Proteinase" *Science* 248:358361.

Roberts, N. A., (1995) "Drug-resistance patterns of saquinavir and other HIV proteinase inhibitors," *AIDS.9* (supp 2) S27-S32.

Rusconi, Stefano. et al. (2000): "Susceptibility to PNU-140690 (Tipranavir) of Human Immunodeficiency Virus Type 1 Isolates Derived From Patients with Multidrug Resistance to Other Protease Inhibitors," *Antimicrobial Agents and Chemotherapy*, 44(5): 1328-32.

Sadler, et al., (1999) "Safety and Pharmacokinetics of Amprenavir (141 W94), a Human Immunodeficiency Virus (HIV) Type 1 Protease Inhibitor, Following Oral Administration of Single Doses to HIV-Infected Adults," *Antimicrobial Agents and Chemotherapy*, 43: 1686-1692.

Sarkar, et al., (1990) "The "Megaprimer" Method of Site-Directed Mutagenesis," *BioTech* 8(4):404-407.

Schuurman, et al., (1999), "Worldwide Evaluation of DNA Sequencing Approaches for Identification of Drug Resistance Mutations in the Human Immunodeficiency Virus Type 1 Reverse Transcriptase," *Journal of Clinical Microbiology*, 37(7): 2291-2296.

Shi, et al., (1997), "A Recombinant Retroviral System for Rapid In Vivo Analysis of Human Immunodeficiency Virus Type 1 Susceptibility to reverse Transcriptase Inhibitors," *Antimicrobial Agents and Chemotherapy*, 41(12): 2781-85.

Smidt, et al., (1996) "A Mutation in Human Immunodeficiency Virus Type 1 Protease at Position 88, Located Outside the Active Site, Confers Resistance to the Hydroxyethylurea Inhibitor SC-55389A," *Antimicrobial Agents and Chemotherapy*, 41: 515-522.

St. Clair, et al., (1996) "In Vitro Antiviral Activity of 141 W94 (VX-478) in Combination with Other Antiretroviral Agents," *Antiviral Research* 29: 53-56.

Tian, et al., (1998) "Zidovudine/Lamivudine Co-resistance Is Preceded by a Transient Period of Zidovudine Hypersensitivity," 2nd International Workshop on HIV Drug Resistance and Treatment Strategies, Abstract 30.

Tisdale, M. et al. (1995): "Cross-Resistance Analysis of Human Immunodeficiency Virus Type 1 Variants Individually Selected for Resistance to Five Different Protease Inhibitors," *Antimicrobial Agents and Chemotherapy* 39(8):1704-10.

Tisdale, M. et al. (1998): "Genotypic and phenotypic analysis of HIV from patients on ZDV/3TC/amprenavir combination therapy," *Int. Conf AIDS* 12:583 (Abstract No. 32312).

Tucker, et al., (1998) "Estimate of the Frequency of Human Immunodeficiency Virus Type 1 Protease Inhibitor Resistance Within Unselected Virus Populations In Vitro," *Antimicrobial Agents and Chemotherapy*, 42: 478-480.

Young et al. J. Infect. Disease 178(5) 1497-1501 (1998).

Ziermann, et al.,(2000), "A Mutation in Human Immunodeficiency Virus Type 1 Protease, N88S, That Causes In Vitro Hypersensitivity to Amprenavir," *Journal of Virology*, 74(9): 4414-4419.

* cited by examiner

LPV Phenotype vs. Mutation Score

**LPV Phenotype vs. Mutation Score
I54A, L, M, S, T, V**

N=1402

PT-R, GT-S

PT-S, GT-R

Log (LPV fold change)

LPV Mutation Score

SEQ. ID. NO: 1: NL4-3 HIV Protease Amino Acid Sequence

PQITLWQRPL VTIKIGGQLK EALLDTGADD TVLEEMNLPG RWKPKMIGGI
GGFIKVRQYD QILIEICGHK AIGTVLVGPT PVNIIGRNLL TQIGCTLNF

FIGURE 12B

SEQ. ID. NO: 2: NL4-3 HIV Protease Gene Nucleotide Sequence 1-10   cct cag atc act ctt tgg cag cga ccc ctc 11-20  gtc aca ata aag ata ggg ggg caa tta aag 21-30  gaa gct cta tta gat aca gga gca gat gat 31-40  aca gta tta gaa gaa atg aat ttg cca gga 41-50  aga tgg aaa cca aaa atg ata ggg gga att 51-60  gga ggt ttt atc aaa gta aga cag tat gat 61-70  cag ata ctc ata gaa atc tgc gga cat aaa 71-80  gct ata ggt aca gta tta gta gga cct aca 81-90  cct gtc aac ata att gga aga aat ctg ttg 91-99  act cag att ggc tgc act tta aat ttt

Effect of Amino Acid at Position 54

FIGURE 14

COMPOSITIONS AND METHODS FOR DETERMINING THE SUSCEPTIBILITY OF A PATHOGENIC VIRUS TO PROTEASE INHIBITORS

This application is entitled to and claims priority to U.S. Provisional Application Nos. 60/357,171, filed Feb. 15, 2002; 60/359,342, filed Feb. 22, 2002; and 60/392,377, filed Jun. 26, 2002, the contents of which are hereby incorporated by reference in their entireties.

1. FIELD OF INVENTION

This invention relates to compositions and methods for determining the susceptibility of a pathogenic virus to an anti-viral compound. The compositions and methods are useful for identifying effective drug regimens for the treatment of viral infections, and identifying and determining the biological effectiveness of potential therapeutic compounds.

2. BACKGROUND OF THE INVENTION

More than 60 million people have been infected with the human immunodeficiency virus ("HIV"), the causative agent of acquired immune deficiency syndrome ("AIDS"), since the early 1980s. See Lucas, 2002, Lepr Rev. 73(1): 64-71. HIV/AIDS is now the leading cause of death in sub-Saharan Africa, and is the fourth biggest killer worldwide. At the end of 2001, an estimated 40 million people were living with HIV globally. See Norris, 2002, Radiol Technol. 73(4):339-363.

Modern anti-HIV drugs target different stages of the HIV life cycle and a variety of enzymes essential for HIV's replication and/or survival. Amongst the drugs that have so far been approved for AIDS therapy are nucleoside reverse transcriptase inhibitors such as AZT, ddI, ddC, d4T, 3TC, abacavir, nucleotide reverse transcriptase inhibitors such as tenofovir, non-nucleoside reverse transcriptase inhibitors such as nevirapine, efavirenz, delavirdine and protease inhibitors such as saquinavir, ritonavir, indinavir, nelfinavir, amprenavir and lopinavir.

One consequence of the action of an anti-viral drug is that it can exert sufficient selective pressure on virus replication to select for drug-resistant mutants (Herrmann et al., 1977, Ann NY Acad Sci 284:632-637). With increasing drug exposure, the selective pressure on the replicating virus population increases to promote the more rapid emergence of drug resistant mutants.

With the inevitable emergence of drug resistance, strategies must be designed to optimize treatment in the face of resistant virus populations. Ascertaining the contribution of drug resistance to drug failure is difficult because patients that are likely to develop drug resistance are also likely to have other factors that predispose them to a poor prognosis (Richman, 1994, AIDS Res Hum Retroviruses 10:901-905). In addition, each patient typically harbors a diverse mixture of mutant strains of the virus with different mutant strains having different susceptibilities to anti-viral drugs.

The traditional tools available to assess anti-viral drug resistance are inadequate; the classical tests for determining the resistance of HIV to an anti-viral agent are complex, time-consuming, expensive, potentially hazardous and not custom tailored to the treatment of a given patient. See Barre-Sinoussi et al., 1983, Science 220:868-871; Popovic et al., 1984, Science 224:497-500), and variations of it (see, e.g., Goedert et al., 1987, JAMA 257:331-334; Allain et al., 1987, N. Engl. J. Med. 317:1114-1121; Piatak et al., 1993, Science 259:1749-1754; Urdea, 1993, Clin. Chem. 39:725-726; Kellam and Larder, 1994, Antimicrobial Agents and Chemo. 38:23-30.

Two general approaches are now used for measuring resistance to anti-viral drugs. The first, called phenotypic testing, directly measures the susceptibility of virus taken from an infected person's virus to particular anti-viral drugs. Petropoulos et al., 2000, Antimicrob. Agents Chemother. 44:920-928 and Hertogs et al., 1998, Antimicrob Agents Chemother 42(2):269-76 provide a description of phenotypic assays in widespread use today. Gunthard et al., 1998, AIDS Res Hum Retroviruses 14:869-76 and Schuurman et al., 1999, J Clin Microbiol. 37:2291-96 discuss currently prevalent genotypic assays. Hirsch et al., 2000, JAMA 283: 2417-26 provide a general analysis of the currently available assays for testing drug susceptibility.

The second method, called genotypic testing, detects mutations in the virus that affect drug susceptibility and can associate specific genetic mutations with drug resistance and drug failure. Genotypic testing examines virus taken from a patient, looking for the presence of specific genetic mutations that are associated with resistance to certain drugs. Genotypic testing has a few advantages over phenotypic testing, most notably the relative simplicity and speed with which the test can be performed. The testing can take as little as a few days to complete, and because it is less complex, it is somewhat cheaper to perform. However, interpretation of genotypic data is dependent on previous knowledge of the relationships between specific mutations and changes in drug susceptibility.

Carrillo et al., 1998, J. Virol. 72:7532-41 describe the in vitro selection and characterization of HIV-1 variants having reduced susceptibility to lopinavir. Nine different mutations at 8 amino acid positions were associated with reduced susceptibility to lopinavir. A subsequent study found 23 different mutations at 11 positions in the HIV protease that correlated with reduced in vitro susceptibility to lopinavir in plasma samples of HIV-infected patients who had been treated previously with at least one protease inhibitor (Kempf et al., 2001, J. Virol. 75:7462-69). A crude algorithm that attempted to correlate the phenotypic resistance to lopinavir with the number of mutations observed at the 11 identified positions, and therefore to predict the effectiveness of lopinavir treatment, was postulated (Kempf et al., 2000, Antiviral Therapy 5 (suppl. 3):70, abstract 89). According to the algorithm, a virus was susceptible to treatment with lopinavir if it had five or fewer mutations at the 11 identified positions in its protease. If the number of mutations at these 11 positions was six or more, then the virus was predicted to be resistant to lopinavir treatment. Id.

Efforts to date to use genotypic correlates of reduced susceptibility to predict the effectiveness of anti-viral drugs, especially drugs targeted against the ever-evolving HIV are, at best, imperfect. An algorithm that can more accurately predict whether a given anti-viral drug or combination of drugs would be effective in treating a given patient would save time and money by identifying drugs that are not likely to succeed before they are administered to the patient. More importantly, it would improve the quality of life of the patient by sparing him or her the trauma of treatment with potent toxins that result in no improvement with respect to his or her HIV infection. Therefore, an urgent need exists for a more accurate algorithm for predicting whether a particular drug would be effective for treating a particular patient. Moreover, a genotype based assay can be faster and more cost effective than phenotypic assays.

3. SUMMARY OF THE INVENTION

The present invention provides methods and compositions for developing and using algorithms for determining the effectiveness of an anti-viral therapy or combination of therapies. The algorithms are based on an analysis of paired phenotypic and genotypic data guided by phenotypic clinical cut-offs (the point at which resistance to a therapy begins and sensitivity ends). The algorithms significantly improve the quality of life of a patient by accurately predicting whether a given anti-viral drug would be effective in treating the patient, thereby sparing him or her the trauma of treatment with potent toxins that result in no improvement in his or her HIV infection.

In one aspect, the present invention provides algorithms that allow one to provide a patient with an effective treatment regimen by predicting whether an infected individual will respond to treatment with an anti-viral agent or combination of agents, thereby allowing an effective treatment regimen to be designed without subjecting the patient to unnecessary side effects. Also, by avoiding the administration of ineffective drugs, considerable time and money is saved.

In another aspect, the present invention provides methods for determining the susceptibility of a virus to an anti-viral treatment, comprising detecting, in the viral genome or viral enzymes, the presence or absence of mutations associated with reduced susceptibility to the anti-viral treatment.

In another aspect, the present invention provides methods for determining the effectiveness of an anti-viral treatment of an individual infected with a virus, comprising detecting, in a sample from said individual, the presence or absence of mutations associated with reduced susceptibility to the anti-viral treatment.

The present invention also provides methods of monitoring the clinical progression of viral infection in individuals receiving an anti-viral treatment by determining, as described above, the effectiveness of the same or a different anti-viral treatment.

In one embodiment, the present invention provides nucleic acids and polypeptides comprising a mutation in the protease of a human immunodeficiency virus ("HIV") associated with reduced susceptibility to a protease inhibitor. Examples of protease inhibitors include, but are not limited to, saquinavir, ritonavir, indinavir, nelfinavir, amprenavir and lopinavir. In one embodiment, the protease inhibitor is lopinavir.

In one aspect, the invention provides a method for determining whether a human immunodeficiency virus is likely to be resistant or susceptible to treatment with a protease inhibitor, comprising: detecting, in said HIV, the presence or absence of one or more of the HIV protease mutations listed in Table 7, assigning a weighting factor to each mutation as provided in Table 7, and adding said weighting factors to get a total score for said individual wherein said individual is likely to be resistant to treatment with said protease inhibitor if said total score is equal to or greater than a cut-off score and said individual is likely to be susceptible to treatment with said protease inhibitor if said total score is less than said cut-off score. In one embodiment, the cut-off score is 6. In another embodiment, the cut-off score is 7. In another embodiment, the cut-off score is 8.

In another aspect, the invention provides a method for determining whether a human immunodeficiency virus has an increased likelihood of having reduced susceptibility to treatment with a protease inhibitor, comprising: detecting, in said HIV, the presence or absence of one or more of the HIV protease mutations listed in Table 7; assigning a weighting factor to each mutation as provided in Table 7; and adding said weighting factors to get a total score for said HIV, wherein said HIV has an increased likelihood of being resistant to treatment with said protease inhibitor if said total score is equal to or greater than a cut-off score. In one embodiment, the cut-off score is 6. In another embodiment, the cut-off score is 7. In another embodiment, the cut-off score is 8.

In another aspect, the invention provides a method for determining whether an individual infected with a human immunodeficiency virus is likely to be resistant or susceptible to treatment with a protease inhibitor, comprising: detecting, in a sample from said individual, the presence or absence of one or more of the HIV protease mutations listed in Table 7, assigning a weighting factor to each mutation as provided in Table 7, and adding said weighting factors to get a total score for said individual wherein said individual is likely to be resistant to treatment with said protease inhibitor if said total score is equal to or greater than a cut-off score and said individual is likely to be susceptible to treatment with said protease inhibitor if said total score is less than said cut-off score. In one embodiment, the cut-off score is 6. In another embodiment, the cut-off score is 7. In another embodiment, the cut-off score is 8.

In another aspect, the invention provides a method for determining whether a HIV has an increased likelihood of having a reduced susceptibility to treatment with a protease inhibitor, comprising detecting in the protease of said HIV or in a nucleic acid of said HIV that encodes the protease, the presence or absence of a mutation associated with reduced susceptibility to treatment with said protease inhibitor at amino acid position 20, 33, 34, 43, 46, 48, 50, 54, 55, 58, 63, 66, 73, 74, 76, 79, 82, 84 or 89 of the amino acid sequence of said protease, wherein the presence of said mutation indicates that the HIV has an increased likelihood of having reduced susceptibility to treatment with the protease inhibitor, with the proviso that said mutation is not K20M, K20R, M46I, M46L, I54L, I54T, I54V, L63P, V82A, V82F, V82T or I84V. In one embodiment, the mutation is detected in the protease of said HIV. In another embodiment, the mutation is detected in a nucleic acid of said HIV that encodes the protease.

In another embodiment, the mutation associated with reduced susceptibility to treatment with said protease inhibitor is at amino acid position 20, 33, 34, 46, 50, 54, 63, 66, 73, 74, 76, 79, 82, 84 or 89 of the amino acid sequence of said protease, with the proviso that said mutation is not K20M, K20R, L33F, L33M, K43T, M46I, M46L, I50V, I54A, I54L, I54M, I54S, I54T, I54V, L63P, G73A, G73S, G73T, T74S, V82A, V82F, V82I, V82S, V82T or I84V.

In another embodiment, the mutation associated with reduced susceptibility to treatment with said protease inhibitor is at amino acid position 10, 11, 32, 47, 53, 71 or 95 of the amino acid sequence of said protease, with the proviso that said mutation is not V32I or I47V. In one embodiment, the mutation associated with reduced susceptibility to treatment with said protease inhibitor is selected from the group consisting of: L10F, F53L and A71L.

In another embodiment, the mutation associated with reduced susceptibility to treatment with said protease inhibitor is selected from the group consisting of: K20I, M46V, I50L, I54A, I54M, I54S, L63T, V82S, I84A, I84L, L33F, L33I, L33V, E34D, E34K, E34Q, K43T, G48V, I50L, I50V, K55R, Q58E, G73C, G73T, T74A, T74P, T74S, L76V, P79A, P79D, P79E, L89I and L89M. In another embodiment, the mutation is selected from the group consisting of:

K20I, M46V, I50L, L63T, I84A, I84L, L33I, L33V, E34D, E34K, E34Q, I50V, I54M, G73C, T74A, T74P, L76V, P79A, P79D, P79E, L89I and L89M. In another embodiment, the mutation is selected from the group consisting of: K20I, M46V, I50L, L63T, I84A, I84L, L33I, L33V, E34D, E34K, E34Q, G73C, T74A, T74P, L76V, P79A, P79D, P79E, L89I and L89M.

In another aspect, the invention provides a method for determining whether an individual infected with HIV has an increased likelihood of having a reduced susceptibility to treatment with a protease inhibitor, comprising detecting, in a sample from said individual, the presence or absence of a mutation associated with reduced susceptibility to treatment with said protease inhibitor at amino acid position 20, 33, 34, 43, 46, 48, 50, 54, 55, 58, 63, 66, 73, 74, 76, 79, 82, 84 or 89 of the amino acid sequence of the protease of the HIV, wherein the presence of said mutation indicates that the individual has an increased likelihood of having reduced susceptibility to treatment with the protease inhibitor, with the proviso that said mutation is not K20M, K20R, M46I, M46L, I54L, I54T, I54V, L63P, V82A, V82F, V82T or I84V. In one embodiment, the mutation is detected in the protease of said HIV. In another embodiment, the mutation is detected in a nucleic acid of said HIV that encodes the protease.

In another embodiment, the mutation associated with reduced susceptibility to treatment with said protease inhibitor is at amino acid position 20, 33, 34, 46, 50, 54, 63, 66, 73, 74, 76, 79, 82, 84 or 89 of the amino acid sequence of the protease of the HIV, with the proviso that said mutation is not K20M, K20R, L33F, L33M, K43T, M46I, M46L, I50V, I54A, I54L, I54M, I54S, I54T, I54V, L63P, G73A, G73S, G73T, T74S, V82A, V82F, V82I, V82S, V82T or I84V.

In another embodiment, the mutation associated with reduced susceptibility to treatment with said protease inhibitor is at amino acid position 10, 11, 32, 47, 53, 71 or 95 of the amino acid sequence of the protease of the HIV, with the proviso that said mutation is not V32I or I47V. In one embodiment, the mutation associated with reduced susceptibility to treatment with said protease inhibitor is selected from the group consisting of: L10F, F53L and A71L.

In another embodiment, the mutation associated with reduced susceptibility to treatment with said protease inhibitor is selected from the group consisting of: K20I, M46V, I50L, I54A, I54M, I54S, L63T, V82S, I84A, I84L, L33F, L33I, L33V, E34D, E34K, E34Q, K43T, G48V, I50L, I50V, K55R, Q58E, G73C, G73T, T74A, T74P, T74S, L76V, P79A, P79D, P79E, L89I and L89M. In another embodiment, the mutation is selected from the group consisting of: K20I, M46V, I50L, L63T, I84A, I84L, L33I, L33V, E34D, E34K, E34Q, I50V, I54M, G73C, T74A, T74P, L76V, P79A, P79D, P79E, L89I and L89M. In another embodiment, the mutation is selected from the group consisting of: K20I, M46V, I50L, L63T, I84A, I84L, L33I, L33V, E34D, E34K, E34Q, G73C, T74A, T74P, L76V, P79A, P79D, P79E, L89I and L89M.

In another embodiment, the human immunodeficiency virus is human immunodeficiency virus type 1 ("HIV-1").

In another aspect, the invention provides an isolated oligonucleotide encoding a protease in a HIV that comprises a mutation at amino acid position 20, 33, 34, 43, 46, 48, 50, 54, 55, 58, 63, 66, 73, 74, 76, 79, 82, 84 or 89 of an amino acid sequence of said protease in said human immunodeficiency virus, wherein the mutation is associated with reduced susceptibility to a protease inhibitor, with the proviso that said mutation is not K20M, K20R, M46I, M46L, I54L, I54T, I54V, L63P, V82A, V82F, V82T or I84. In one embodiment, the oligonucleotide is between about 10 and about 100 nucleotides long. In another embodiment, the oligonucleotide is between about 10 and about 90 nucleotides long. In another embodiment, the oligonucleotide is between about 10 and about 80 nucleotides long. In another embodiment, the oligonucleotide is between about 10 and about 70 nucleotides long. In another embodiment, the oligonucleotide is between about 10 and about 60 nucleotides long. In another embodiment, the oligonucleotide is between about 10 and about 50 nucleotides long. In another embodiment, the oligonucleotide is between about 10 and about 40 nucleotides long. In another embodiment, the oligonucleotide is between about 10 and about 30 nucleotides long. In another embodiment, the oligonucleotide is between about 10 and about 20 nucleotides long.

In another embodiment, the isolated oligonucleotide comprises mutation associated with reduced susceptibility to a protease inhibitor at amino acid position 20, 33, 34, 43, 46, 48, 50, 54, 55, 58, 63, 66, 73, 74, 76, 79, 82, 84 or 89 of an amino acid sequence of said protease in said HIV with the proviso that said mutation is not K20M, K20R, L33F, L33M, K43T, M46I, M46L, I50V, I54A, I54L, I54M, I54S, I54T, I54V, L63P, G73A, G73S, G73T, T74S, V82A, V82F, V82I, V82S, V82T or I84V. The oligonucleotide can be between about 10 and about 100, between about 10 and about 90, between about 10 and about 80, between about 10 and about 70, between about 10 and about 60, between about 10 and about 50, between about 10 and about 40, between about 10 and about 30 or between about 10 and about 20 nucleotides long.

In another embodiment, the isolated oligonucleotide encodes a protease in a HIV that comprises a mutation at codon 20, 33, 34, 43, 46, 48, 50, 54, 55, 58, 63, 66, 73, 74, 76, 79, 82, 84 or 89, wherein the mutation is associated with reduced susceptibility to protease inhibitor, with the proviso that the codons do not encode M or R at position 20, I or L at position 46, L, T or V at position 54, P at position 63, A, F or T at position 82 or V at position 84. The oligonucleotide can be between about 10 and about 100, between about 10 and about 90, between about 10 and about 80, between about 10 and about 70, between about 10 and about 60, between about 10 and about 50, between about 10 and about 40, between about 10 and about 30 or between about 10 and about 20 nucleotides long.

In another embodiment, the invention provides an isolated oligonucleotide encoding a protease in a HIV that comprises mutations at codon 20, 33, 34, 50, 54, 63, 66, 73, 74, 76, 79, 82 or 89, wherein the mutation is associated with reduced susceptibility to a protease inhibitor, with the proviso that the codons do not encode M or R at position 20, F or M at position 33, I or L at position 46, A, L, S, T or V at position 54, P at position 63, S or T at position 73, S at position 74, A, F or T at position 82 or V at position 84. The oligonucleotide can be between about 10 and about 100, between about 10 and about 90, between about 10 and about 80, between about 10 and about 70, between about 10 and about 60, between about 10 and about 50, between about 10 and about 40, between about 10 and about 30 or between about 10 and about 20 nucleotides long.

In another embodiment, the invention provides a polypeptide that comprises residues 1-10 of the amino acid sequence of SEQ ID NO:1. In another embodiment, the polypeptide comprises residues 11-20 of the amino acid sequence of SEQ ID NO:1. In another embodiment, the polypeptide comprises residues 21-30 of the amino acid sequence of SEQ ID NO:1. In another embodiment, the polypeptide comprises residues 31-40 of the amino acid sequence of SEQ ID NO:1. In another embodiment, the polypeptide comprises residues 41-50 of the amino acid sequence of SEQ ID NO:1. In another embodiment, the polypeptide comprises residues 51-60 of the amino acid sequence of SEQ ID NO:1. In another embodiment, the polypeptide comprises residues 61-70 of the amino acid sequence of SEQ ID NO:1. In another embodiment, the polypeptide comprises residues 71-80 of the amino acid sequence of SEQ ID NO:1. In another embodiment, the polypeptide comprises residues 81-90 of the amino acid sequence of SEQ ID NO:1. In another embodiment, the polypeptide comprises residues 91-99 of the amino acid sequence of SEQ ID NO:1.

In another embodiment, the polypeptide is at least 70%, but less than 100%, identical to a polypeptide having the amino acid sequence of SEQ ID NO:1. In another embodiment, the polypeptide has an amino acid sequence that is at least 80% identical to the amino acid sequence of SEQ ID NO:1. In another embodiment, the polypeptide has an amino acid sequence that is at least 90% identical to the amino acid sequence of SEQ ID NO:1.

In one embodiment, the invention provides a method wherein the presence or absence of a mutation in a protease is detected by hybridization with a sequence-specific oligonucleotide probe to a nucleic acid sequence of human immunodeficiency virus encoding said mutation, wherein the occurrence of hybridization indicates said presence or absence of said mutation.

In another embodiment, the invention provides a method wherein the presence or absence of a mutation in a protease is detected by nucleic acid sequencing.

In one embodiment, the individual is undergoing or has undergone prior treatment with said or different protease inhibitor.

In one embodiment, the amino acid at position 20 of said protease is an amino acid having a neutral, hydrophobic or non-polar side chain. In another embodiment, the amino acid at position 20 of said protease is I. In another embodiment, the amino acid at position 33 of said protease is an amino acid with a neutral, hydrophobic or non-polar side chain. In another embodiment, the amino acid at position 33 of said protease is I, F or V. In another embodiment, the amino acid at position 33 of said protease is I or V. In another embodiment, the amino acid at position 34 of said protease is an amino acid having a basic, polar or hydrophilic side chain. In another embodiment, the amino acid at position 34 of said protease is K. In another embodiment, the amino acid at position 46 of said protease is an amino acid with a neutral, hydrophobic or non-polar side chain. In another embodiment, the amino acid at position 46 of said protease is V. In another embodiment, the amino acid at position 50 of said protease is an amino acid with a neutral, hydrophobic or non-polar side chain. In another embodiment, the amino acid at position 50 of said protease is L or V. In another embodiment, the amino acid at position 54 of said protease is an amino acid with a neutral, hydrophobic, non-polar, hydrophilic or polar side chain. In another embodiment, the amino acid at position 54 of said protease is an amino acid with a neutral, hydrophobic or non-polar side chain. In another embodiment, the amino acid at position 54 of said protease is A or M. In another embodiment, the amino acid at position 54 of said protease is M. In another embodiment, the amino acid at position 54 of said protease is an amino acid with a neutral, hydrophilic or polar side chain. In another embodiment, the amino acid at position 54 of said protease is S. In another embodiment, the amino acid at position 63 of said protease is an amino acid with a neutral, hydrophilic or polar side chain. In another embodiment, the amino acid at position 63 of said protease is T. In another embodiment, the amino acid at position 66 of said protease is an amino acid with a neutral, hydrophobic or non-polar side chain. In another embodiment, the amino acid at position 66 of said protease is F or V. In another embodiment, the amino acid at position 73 of said protease is an amino acid with a neutral, hydrophilic or polar side chain. In another embodiment, the amino acid at position 73 of said protease is C or T. In another embodiment, the amino acid at position 73 of said protease is C. In another embodiment, the amino acid at position 74 of said protease is an amino acid with a neutral, hydrophobic, non-polar, hydrophilic or polar side chain. In another embodiment, the amino acid at position 74 of said protease is an amino acid with a neutral, hydrophobic or non-polar side chain. In another embodiment, the amino acid at position 74 of said protease is A or P. In another embodiment, the amino acid at position 74 of said protease is an amino acid with a neutral, hydrophilic or polar side chain. In another embodiment, the amino acid at position 74 of said protease is S. In another embodiment, the amino acid at position 76 of said protease is an amino acid with a neutral, hydrophobic or non-polar side chain. In another embodiment, the amino acid at position 76 of said protease is V. In another embodiment, the amino acid at position 79 of said protease is an amino acid with a neutral, hydrophobic, non-polar, acidic, hydrophilic or polar side chain. In another embodiment, the amino acid at position 79 of said protease is an amino acid with a neutral, hydrophobic or non-polar side chain. In another embodiment, the amino acid at position 79 of said protease is A. In another embodiment, the amino acid at position 79 of said protease is an amino acid with an acidic, hydrophilic or polar side chain. In another embodiment, the amino acid at position 79 of said protease is D or E. In another embodiment, the amino acid at position 82 of said protease is an amino acid with a neutral, hydrophilic or polar side chain. In another embodiment, the amino acid at position 82 of said protease is S. In another embodiment, the amino acid at position 84 of said protease is an amino acid with a neutral, hydrophobic or non-polar side chain. In another embodiment, the amino acid at position 84 of said protease is L. In another embodiment, the amino acid at position 89 of said protease is an amino acid with a neutral, hydrophobic or non-polar side chain. In another embodiment, the amino acid at position 89 of said protease is I or M. In another embodiment, the amino acid at position 43 of said protease is an amino acid with a neutral, hydrophobic or non-polar side chain. In another embodiment, the amino acid at position 43 of said protease is T. In another embodiment, the amino acid at position 48 of said protease is an amino acid with a neutral, hydrophobic or non-polar side chain. In another embodiment, the amino acid at position 48 of said protease is V. In another embodiment, the amino acid at position 55 of said protease is an amino acid with a basic, hydrophilic or polar side chain. In another embodiment, the amino acid at position 55 of said protease is R. In another embodiment, the amino acid at position 58 of said protease is an amino acid with an acidic, hydrophilic or polar side chain. In another embodiment, the amino acid at position 58 of said protease is E.

In another aspect, the invention provides a method for detecting the presence or absence of a mutation associated with reduced susceptibility to treatment with said protease inhibitor at at least 2, 3, 4, 5, 6, 7, 8, 9, 10, 11, 12, 13, 14, 15, 16, 17, 18 or 19 of the amino acid positions. In one embodiment, the invention provides a method for detecting the presence or absence of a mutation associated with reduced susceptibility to treatment with said protease inhibitor at 2 or more amino acid positions. In another embodiment, the invention provides a method for detecting the presence or absence of a mutation associated with reduced susceptibility to treatment with said protease inhibitor at 3 or more amino acid positions. In another embodiment, the invention provides a method for detecting the presence or absence of a mutation associated with reduced susceptibility to treatment with said protease inhibitor at 4 or more amino acid positions. In another embodiment, the invention provides a method for detecting the presence or absence of a mutation associated with reduced susceptibility to treatment with said protease inhibitor at 5 or more amino acid positions. In another embodiment, the invention provides a method for detecting the presence or absence of a mutation associated with reduced susceptibility to treatment with said protease inhibitor at 6 or more amino acid positions. In another embodiment, the invention provides a method for detecting the presence or absence of a mutation associated with reduced susceptibility to treatment with said protease inhibitor at 7 or more amino acid positions. In another embodiment, the invention provides a method for detecting the presence or absence of a mutation associated with reduced susceptibility to treatment with said protease inhibitor at 8 or more amino acid positions. In another embodiment, the invention provides a method for detecting the presence or absence of a mutation associated with reduced susceptibility to treatment with said protease inhibitor at 9 or more amino acid positions.

In another aspect, the invention provides a method for determining whether a HIV has an increased likelihood of having a reduced susceptibility to treatment with a first protease inhibitor, comprising detecting in the protease of said HIV the presence or absence of a mutation associated with reduced susceptibility to treatment with a second protease inhibitor at amino acid position 10, 11, 32, 33, 34, 43, 46, 47, 48, 50, 54, 58, 71, 76, 79, 82, 84 or 95 of the amino acid sequence of said protease, wherein the presence of said mutation indicates that the HIV has an increased likelihood of having reduced susceptibility to treatment with said first protease inhibitor, with the proviso that said mutation is not V32I, M46I, M46L, I47V, I50V, I54L, I54M, V82A, or I84V. In one embodiment, the first protease inhibitor is lopinavir or amprenavir. In another embodiment, the second protease inhibitor is lopinavir or amprenavir.

In another aspect, the invention provides a method of determining whether an individual infected with HIV has an increased likelihood of having a reduced susceptibility to treatment with a first protease inhibitor, comprising detecting, in a sample from said individual, the presence or absence of a mutation associated with reduced susceptibility to treatment with a second protease inhibitor at amino acid position 10, 11, 32, 33, 34, 43, 46, 47, 48, 50, 54, 58, 71, 76, 79, 82, 84 or 95 of the amino acid sequence of the protease of the HIV, wherein the presence of said mutation indicates that the individual has an increased likelihood of having reduced susceptibility to treatment with said first protease inhibitor, with the proviso that said mutation is not V32I, M46I, M46L, I47V, I50V, I54L, I54M, V82A, or I84V. In one embodiment, the first protease inhibitor is lopinavir or amprenavir. In another embodiment, the second protease inhibitor is lopinavir or amprenavir.

4. BRIEF DESCRIPTION OF THE FIGURES

FIG. 1 is a diagrammatic representation of the genomic structure of HIV-1.

FIG. 2 is a scatter plot that shows the susceptibility to lopinavir (Log lopinavir fold change) of HIV samples obtained from a training data set with 2038 patients as a function of the number of the resistance-associated mutations in the protease. The genotypic "cutoff value" is 6, i.e., a HIV is defined as genotypically resistant to lopinavir if its total score is 6 or greater and genotypically sensitive if its total score is less than 6.

FIG. 3 is a scatter plot that shows the susceptibility to lopinavir (Log lopinavir fold change) of HIV samples as a function of the number of the resistance-associated mutations in the protease after the removal of samples containing mixtures of amino acids at any of the positions associated with reduced susceptibility to lopinavir. Those samples that contained both a wild-type and a mutant were excluded from the analysis.

FIG. 6 is a scatter plot that shows the susceptibility to lopinavir (Log lopinavir fold change) of HIV samples containing the mutations I54A, L, M, S, T or V in the protease as a function of the total number of the resistance-associated mutations in those samples.

Figure 8:
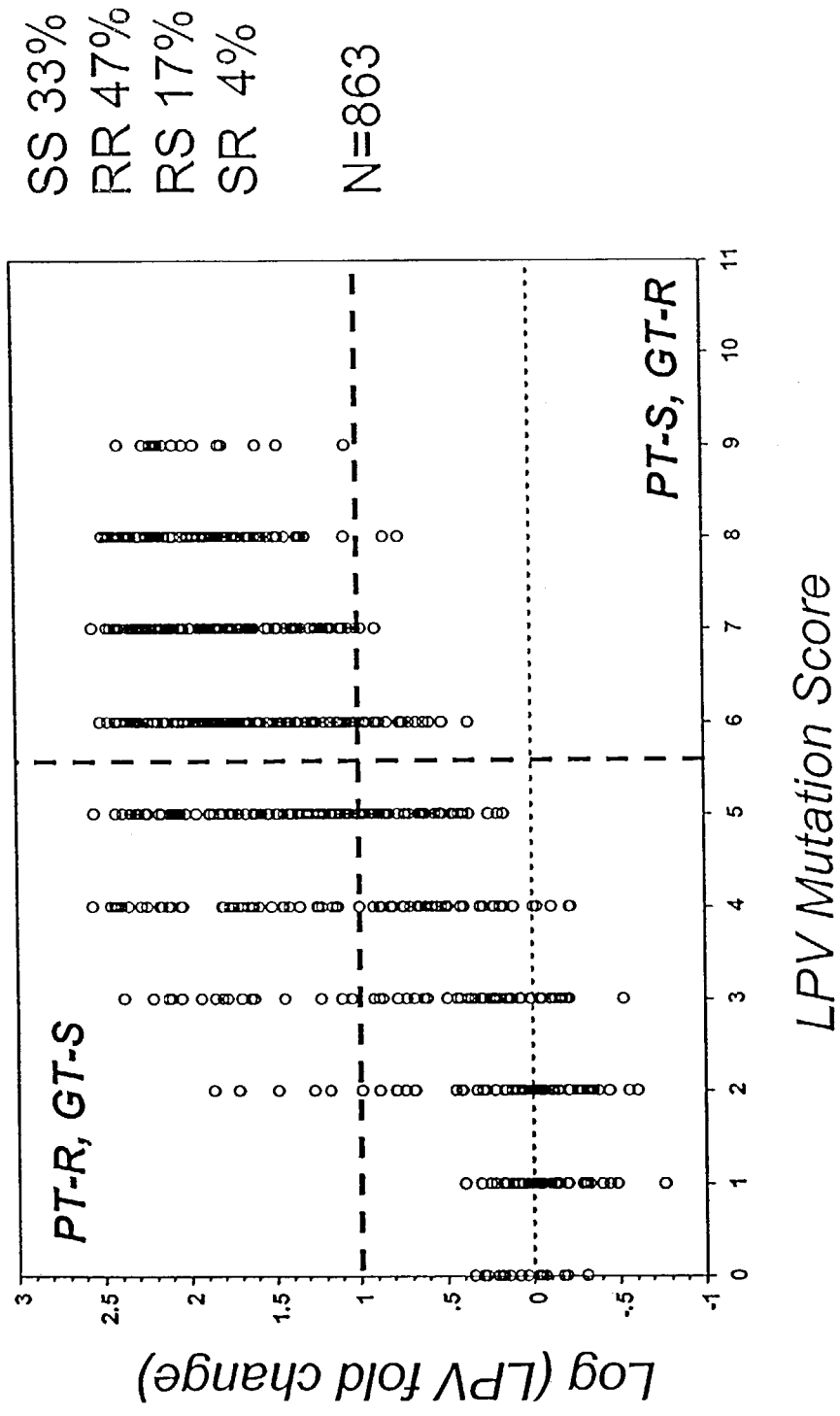

FIG. 8 is a scatter plot that shows the susceptibility to lopinavir (Log lopinavir fold change) of HIV samples as a function of the number of the resistance-associated mutations in the protease after the removal of samples without any primary mutations associated with protease inhibitors and without an $IC_{50}$ fold change ("FC") greater than two for any protease inhibitor and the removal of samples containing mixtures of amino acids at any of the positions associated with reduced susceptibility to lopinavir. Only those samples that contained both, a wild-type or reference strain and a mutant were removed.

Figure 9:
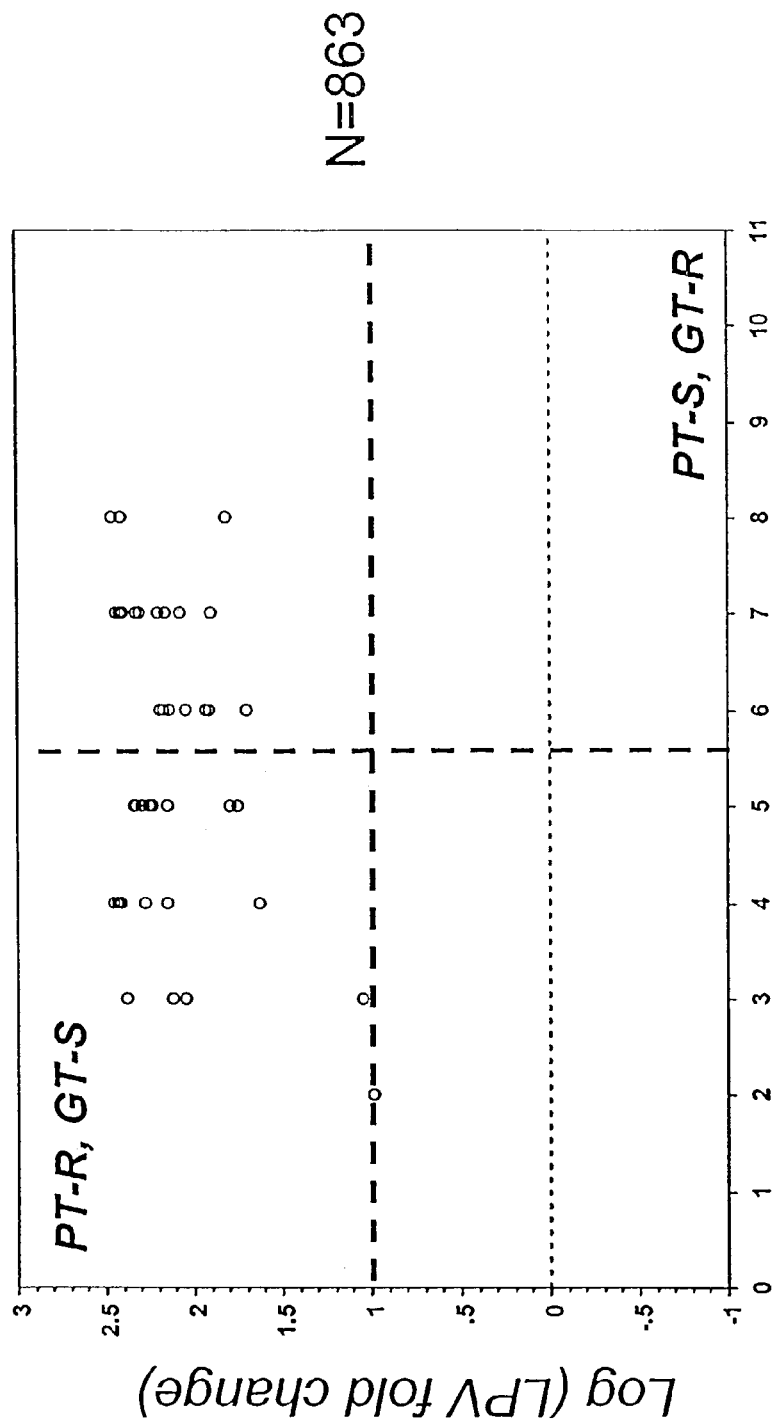

FIG. 9 is a scatter plot that shows the susceptibility to lopinavir (Log lopinavir fold change) of HIV samples containing the mutation I50V in the protease as a function of the total number of the resistance-associated mutations in those samples after the removal of samples without any primary mutations associated with protease inhibitors and without an $IC_{50}$ fold change ("FC") greater than two for any protease inhibitor.

Figure 10:
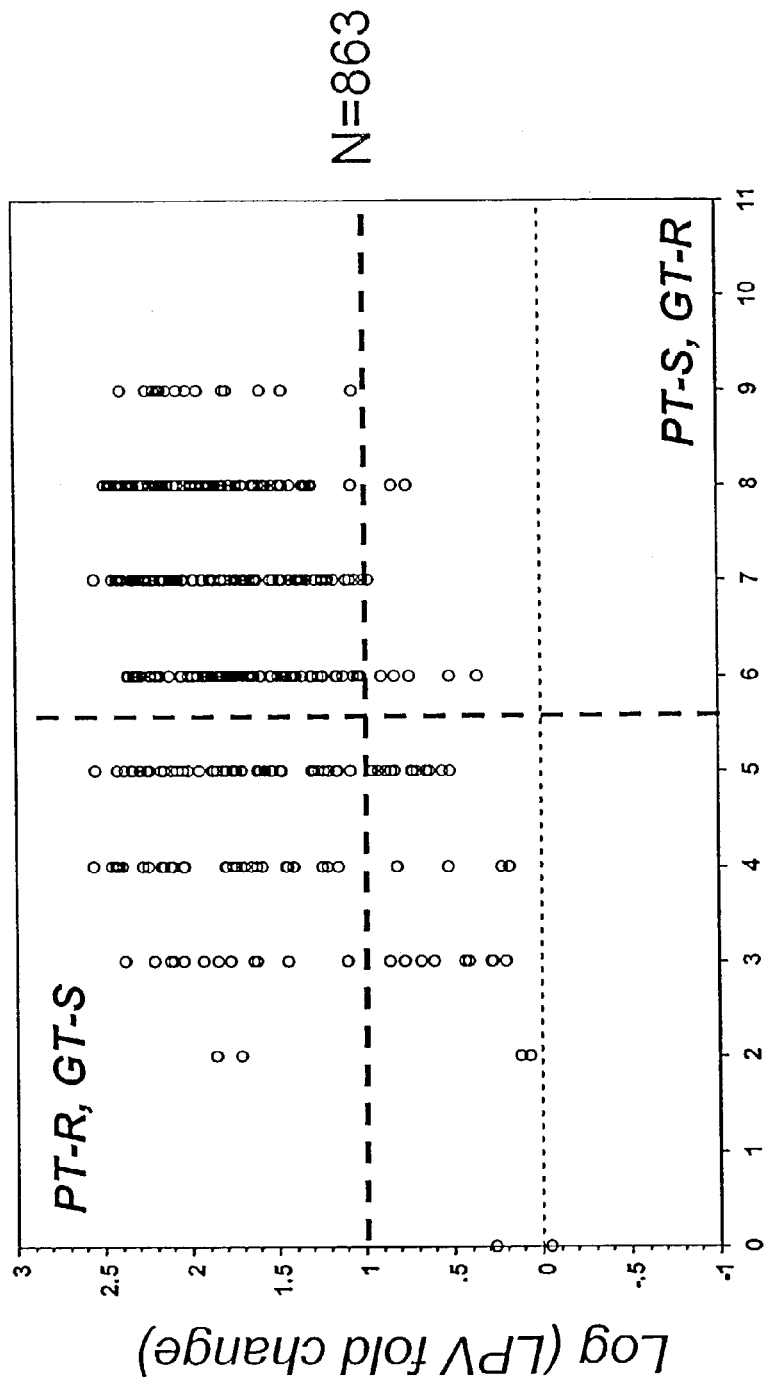

FIG. 10 is a scatter plot that shows the susceptibility to lopinavir (Log lopinavir fold change) of HIV samples containing the mutations V82A, F, S, T or I in the protease as a function of the total number of the resistance-associated mutations in those samples after the removal of samples without any primary mutations associated with protease inhibitors and without an $IC_{50}$ fold change ("FC") greater than two for any protease inhibitor.

Figure 11:
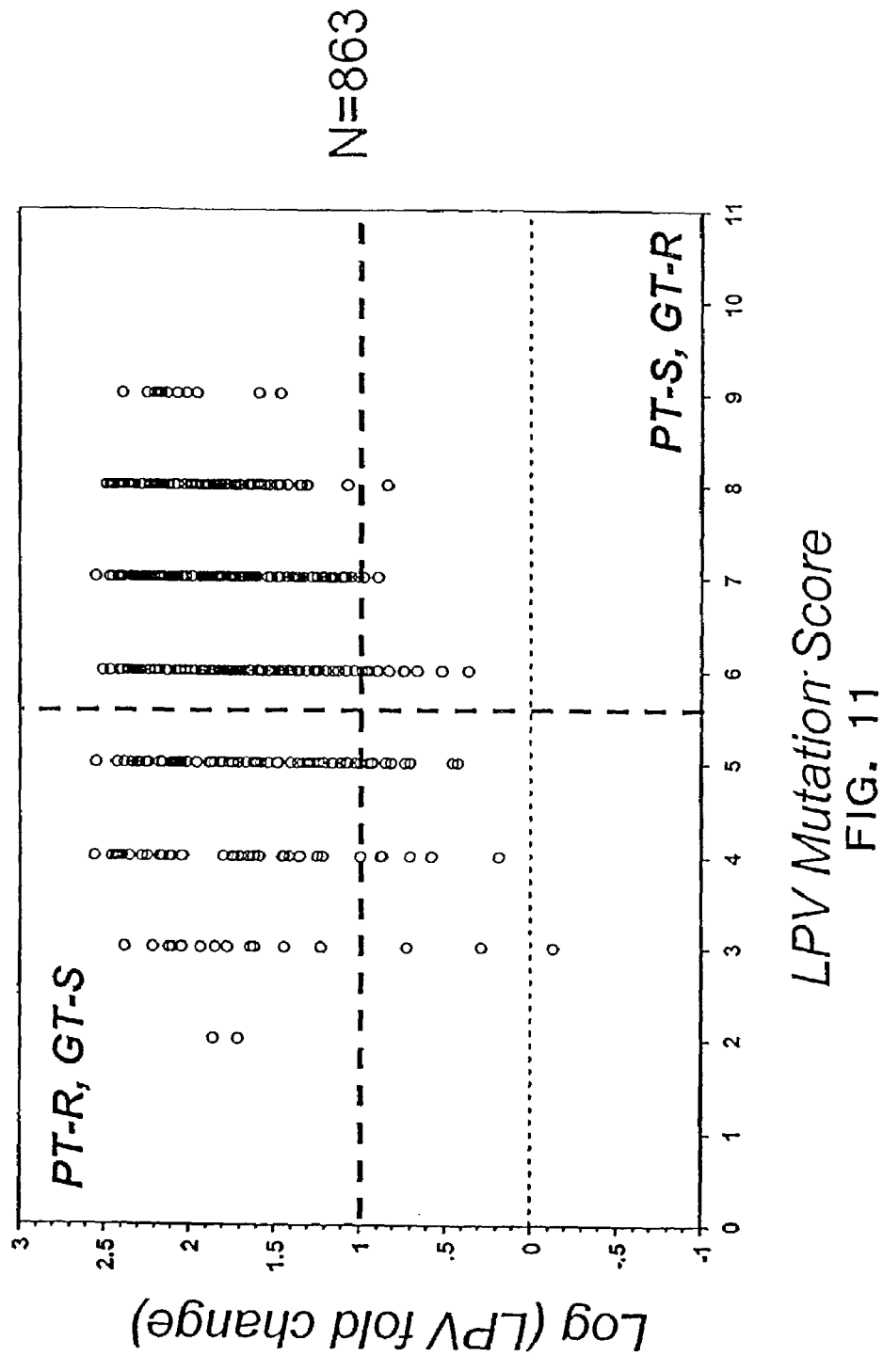

FIG. 11 is a scatter plot that shows the susceptibility to lopinavir (Log lopinavir fold change) of HIV samples containing the mutations I54A, L, M, S, T or V in the protease as a function of the total number of the resistance-associated mutations in those samples after the removal of samples without any primary mutations associated with protease inhibitors and without an $IC_{50}$ fold change ("FC") greater than two for any protease inhibitor.

FIG. 12A shows the amino acid sequence of the NL4-3 HIV (GenBank Accession No. AF324493) protease (SEQ. ID. NO: 1).

FIG. 12B shows the nucleic acid sequence for the NL4-3 HIV (GenBank Accession No. AF324493) protease gene (SEQ. ID. NO: 2).

Figure 13:
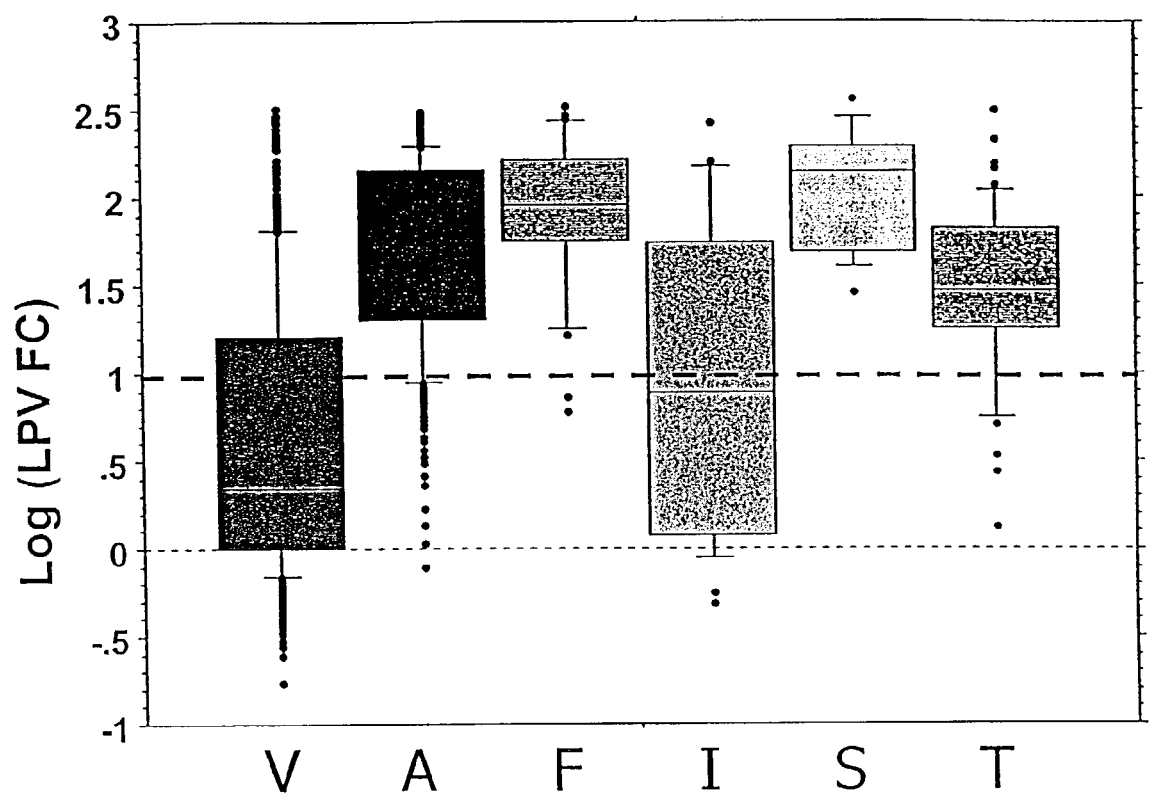

FIG. 13 shows the effect of the amino acid at position 82 on lopinavir fold change. The median (horizontal line), 25th and 75th percentile (box), 10th and 90th percentile (whiskers) and outliers (dots) are shown.

Figure 14:
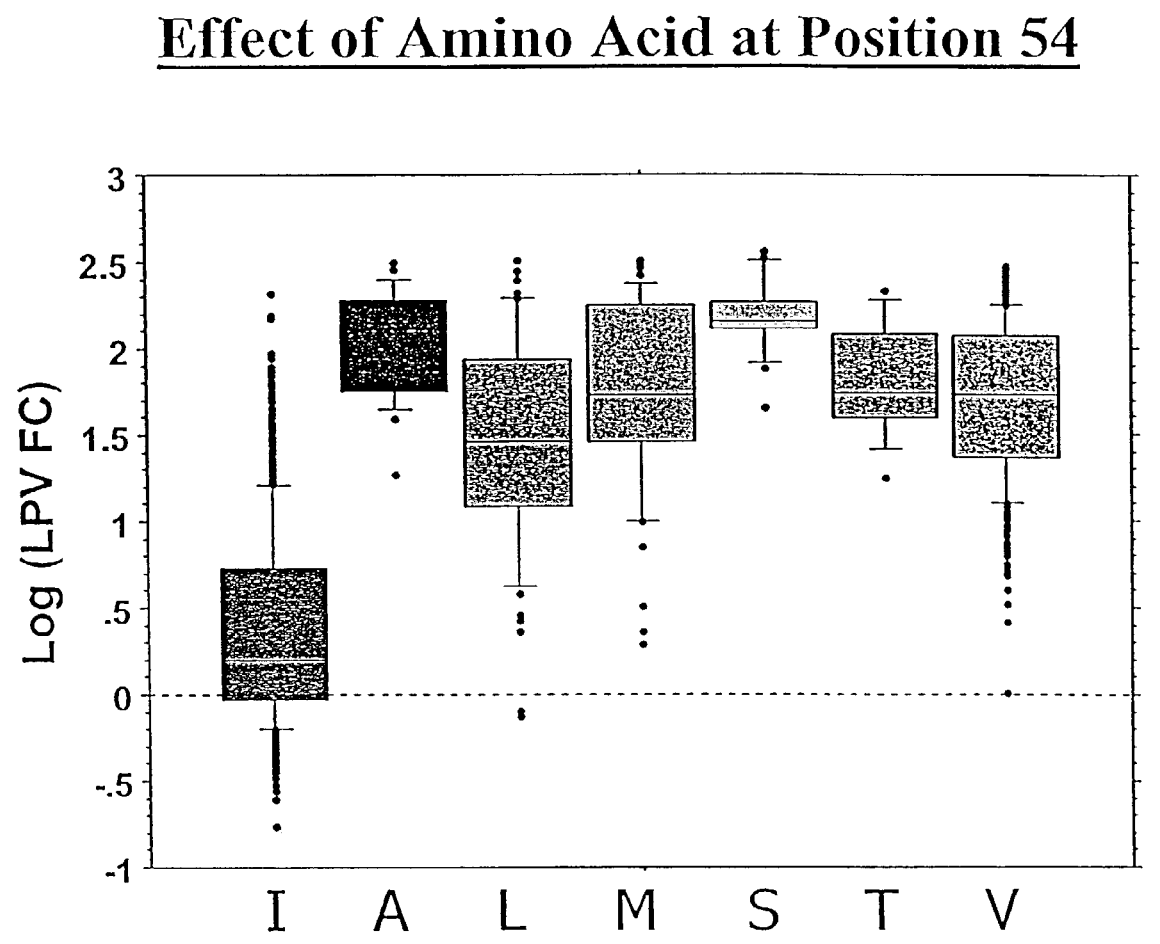

FIG. 14 shows the effect of amino acid at position 54 on lopinavir fold change. The median (horizontal line), 25th and 75th percentile (box), 10th and 90th percentile (whiskers) and outliers (dots) are shown.

Figure 15:
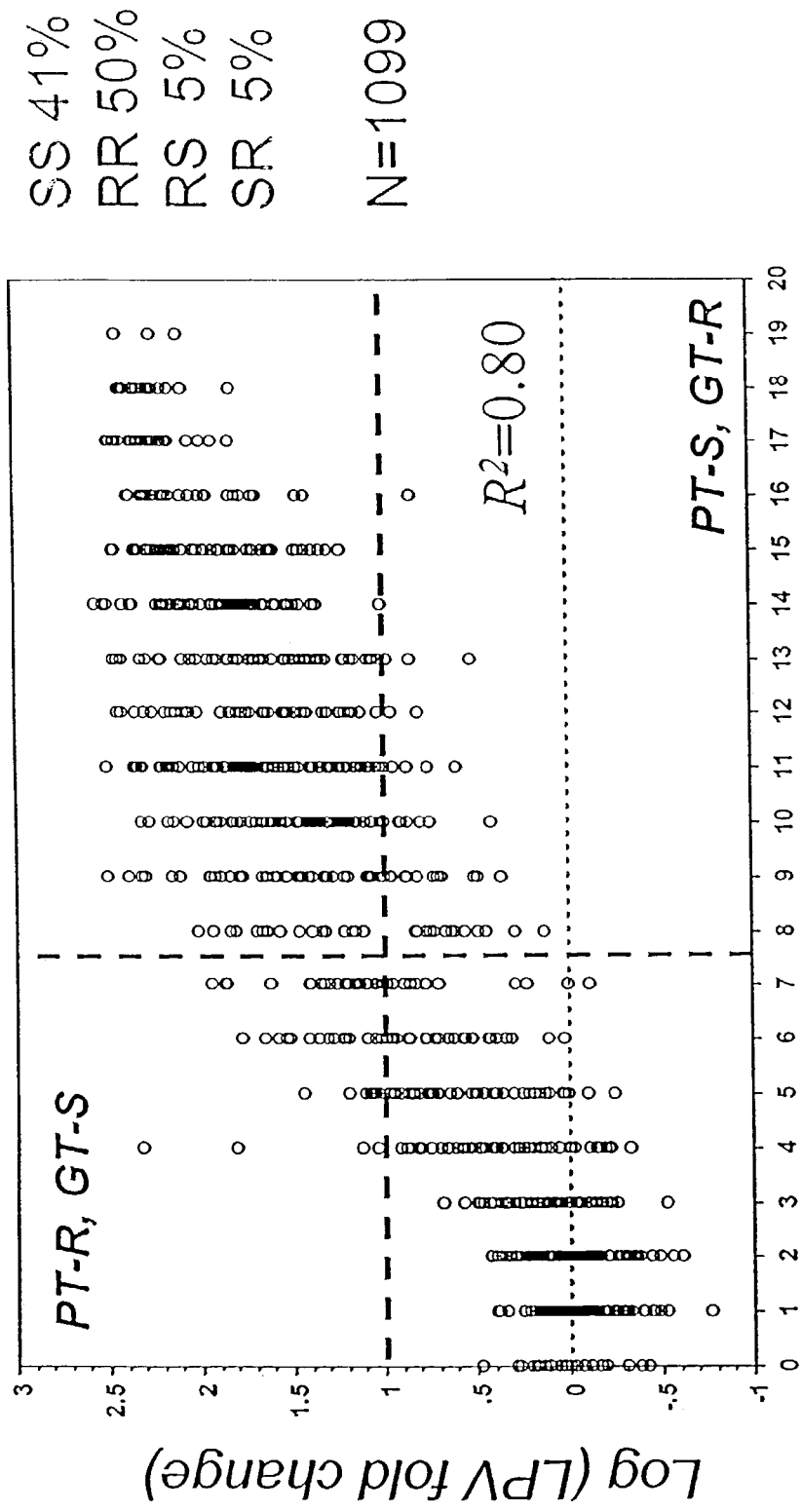

FIG. 15 is a scatter plot that shows the susceptibility to lopinavir (Log lopinavir fold change) of HIV samples obtained from a training data set with 2195 patients as a function of the number of the resistance-associated mutations in the protease. The genotypic "cutoff value" is 8, i.e., a HIV is genotypically resistant to lopinavir if its total score is 8 or greater and genotypically sensitive if its total score is less than 8.

Figure 16:
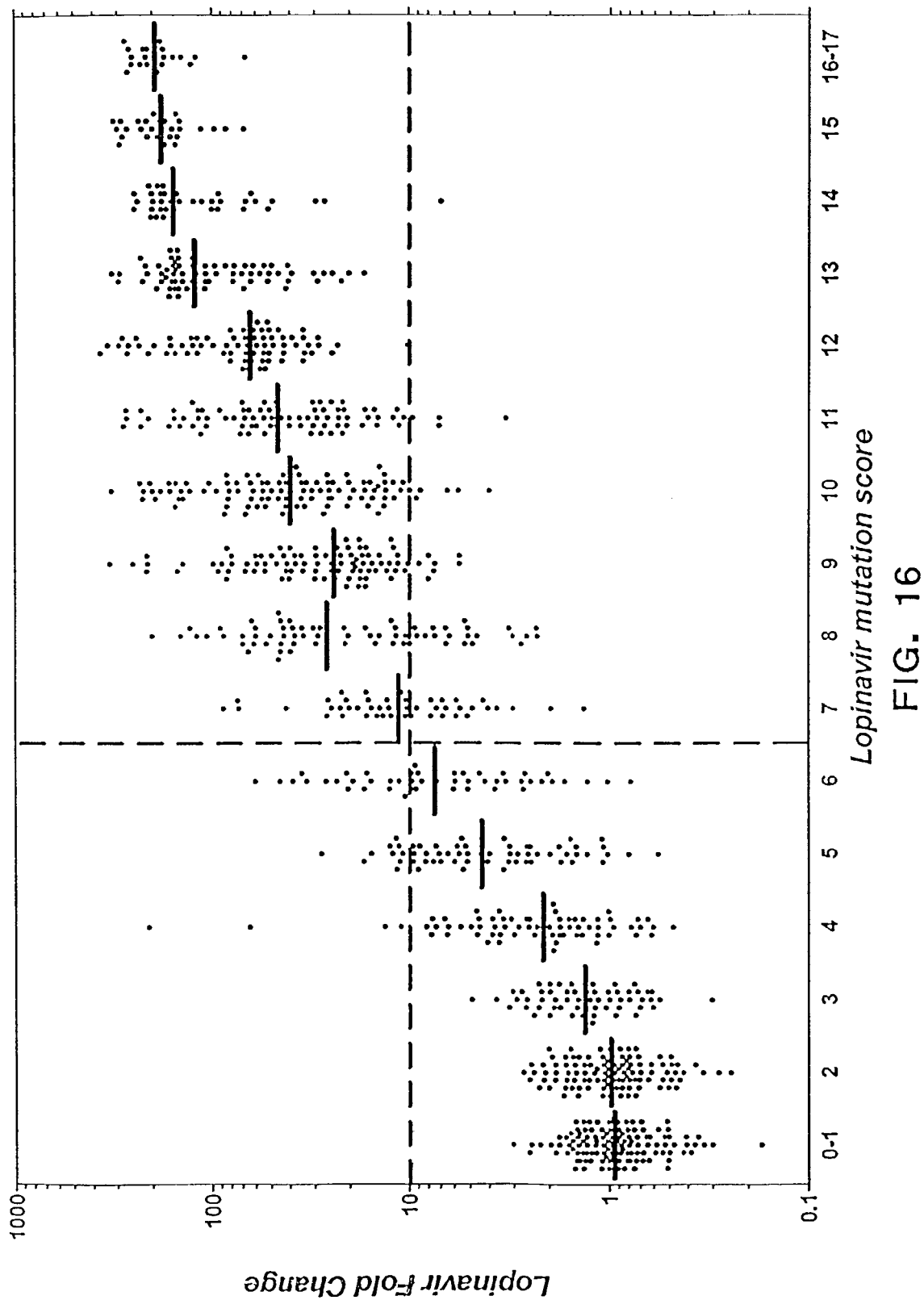

FIG. 16 is a scatter plot that shows the susceptibility to lopinavir (Log lopinavir fold change) of HIV samples obtained from data set of 1099 samples as a function of the number of the resistance-associated mutations in the protease. The genotypic "cutoff value" is 7, i.e., a HIV is genotypically resistant to lopinavir if its total score is 7 or greater and genotypically sensitive if its total score is less than 7.

Figure 17:
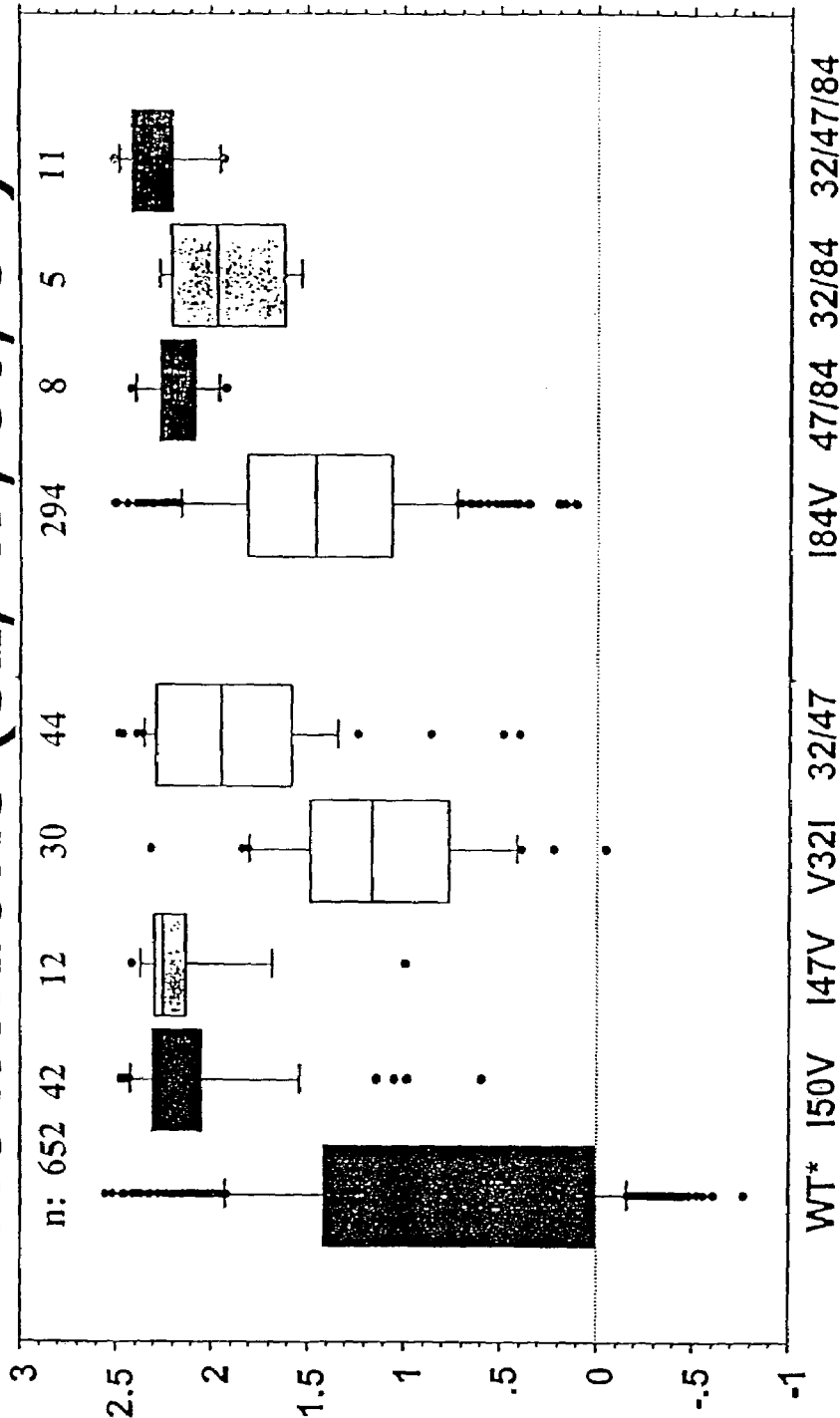

FIG. 17 shows the effect of mutations associated in HIV with resistance to Amprenavir ("APV") on resistance to lopinavir. The median (horizontal line), 25th and 75th percentile (box), 10th and 90th percentile (whiskers) and outliers (dots) are shown.

Figure 18:
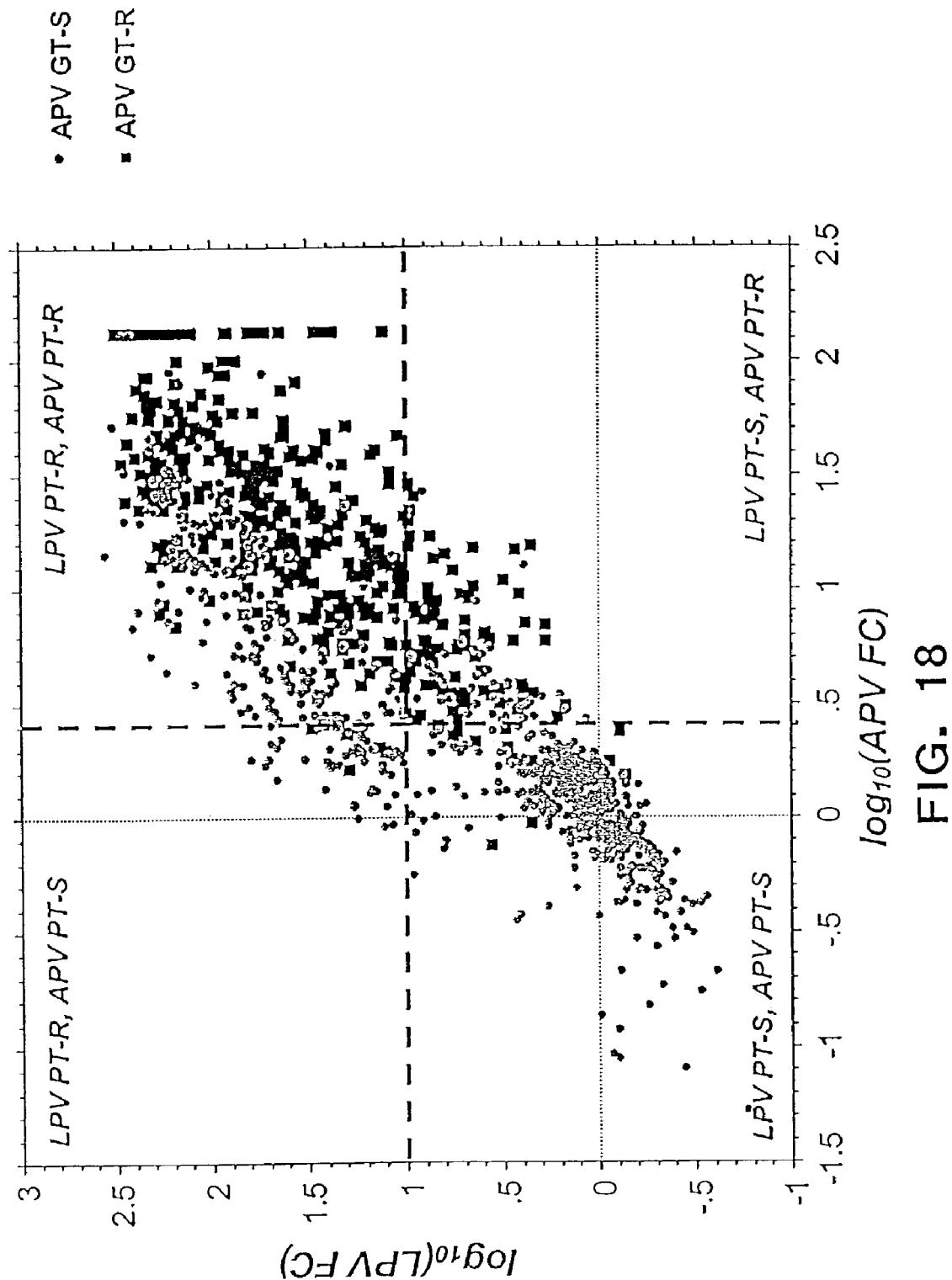

FIG. 18 shows a bivariate scatter plot of lopinavir fold change ("log LPV") versus amprenavir fold change ("log APV").

5. DETAILED DESCRIPTION OF THE INVENTION

The present invention provides methods and compositions for developing an algorithm for determining the effectiveness of anti-viral drugs based on a comprehensive analysis of paired phenotypic and genotypic data guided by phenotypic clinical cut-offs. The present invention also provides methods for determining the susceptibility of a virus to an anti-viral treatment, methods for determining the effectiveness of an anti-viral treatment of an individual infected with a virus, and methods of monitoring the clinical progression of viral infection in individuals receiving antiviral treatment. In another aspect, the present invention also provides nucleic acids and polypeptides comprising a mutation in the protease of a human immunodeficiency virus ("HIV") associated with reduced susceptibility to protease inhibitors, e.g., lopinavir.

5.1 Abbreviations

"LPV" is an abbreviation for the protease inhibitor lopinavir.

"APV" is an abbreviation for the protease inhibitor amprenavir.

"PI" is an abbreviation for protease inhibitor.

"PT-R" and "PT-S" are abbreviations for "phenotypically resistant" and "phenotypically sensitive," respectively.

"GT-R" and "GT-S" are abbreviations for "genotypically resistant" and "genotypically sensitive," respectively.

"PCR" is an abbreviation for "polymerase chain reaction."

"FC" is an abbreviation for "fold change."

The amino acid notations used herein for the twenty genetically encoded L-amino acids are conventional and are as follows:

| Amino Acid | One-Letter Abbreviation | Three Letter Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Unless noted otherwise, when polypeptide sequences are presented as a series of one-letter and/or three-letter abbreviations, the sequences are presented in the N→C direction, in accordance with common practice.

Individual amino acids in a sequence are represented herein as AN, wherein A is the standard one letter symbol for the amino acid in the sequence, and N is the position in the sequence. Mutations within an amino acid sequence are represented herein as $A_1NA_2$, wherein $A_1$ is the standard one letter symbol for the amino acid in the reference protein sequence, $A_2$ is the standard one letter symbol for the amino acid in the mutated protein sequence, and N is the position in the amino acid sequence. For example, a G25M mutation represents a change from glycine to methionine at amino acid position 25. Mutations may also be represented herein as $NA_2$, wherein N is the position in the amino acid sequence and $A_2$ is the standard one letter symbol for the amino acid in the mutated protein sequence (e.g., 25M, for a change from the wild-type amino acid to methionine at amino acid position 25). Additionally, mutations may also be represented herein as $A_1N$, wherein $A_1$ is the standard one letter symbol for the amino acid in the reference protein sequence and N is the position in the amino acid sequence (e.g., G25 represents a change from glycine to any amino acid at amino acid position 25). This notation is typically used when the amino acid in the mutated protein sequence is either not known or, if the amino acid in the mutated protein sequence could be any amino acid, except that found in the reference protein sequence. The amino acid positions are numbered based on the full-length sequence of the protein from which the region encompassing the mutation is derived. Representations of nucleotides and point mutations in DNA sequences are analogous.

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Unless specified otherwise, single-stranded nucleic acid sequences that are represented as a series of one-letter abbreviations, and the top strand of double-stranded sequences, are presented in the 5'→3' direction.

5.2 Definitions

As used herein, the following terms shall have the following meanings:

Unless otherwise specified, "primary mutation" refers to a mutation that affects the enzyme active site, i.e. at those amino acid positions that are involved in the enzyme-substrate complex, or that reproducibly appears in an early round of replication when a virus is subject to the selective pressure of an anti-viral agent, or, that has a large effect on phenotypic susceptibility to an anti-viral agent.

"Secondary Mutation" refers to a mutation that is not a primary mutation and that contributes to reduced susceptibility or compensates for gross defects imposed by a primary mutation.

A "genotypic assay" is a test that determines a genetic sequence of an organism, a part of an organism, a gene or a part of a gene. Such assays are frequently performed in HIV to establish whether certain mutations are associated with drug resistance are present.

As used herein, "genotypic data" are data about the genotype of, for example, a virus. Examples of genotypic data include, but are not limited to, the nucleotide or amino acid sequence of a virus, a part of a virus, a viral gene, a part of a viral gene, or the identity of one or more nucleotides or amino acid residues in a viral nucleic acid or protein.

A "phenotypic assay" is a test that measures the sensitivity of a virus (such as HIV) to a specific anti-viral agent.

"Susceptibility" refers to a virus' response to a particular drug. A virus that has decreased or reduced susceptibility to a drug has an increased resistance or decreased sensitivity to the drug. A virus that has increased or enhanced or greater susceptibility to a drug has an increased sensitivity or decreased resistance to the drug.

Phenotypic susceptibility of a virus to a given drug is a continuum. Nonetheless, it is practically useful to define a threshold or thresholds to simplify interpretation of a particular fold-change result. For drugs where sufficient clinical outcome data have been gathered, it is possible to define a "clinical cutoff value," as below.

"Clinical Cutoff Value" refers to a specific point at which resistance begins and sensitivity ends. It is defined by the drug susceptibility level at which a patient's probability of treatment failure with a particular drug significantly increases. The cutoff value is different for different anti-viral agents, as determined in clinical studies. Clinical cutoff values are determined in clinical trials by evaluating resistance and outcomes data. Drug susceptibility (phenotypic) is measured at treatment initiation. Treatment response, such as change in viral load, is monitored at predetermined time points through the course of the treatment. The drug susceptibility is correlated with treatment response and the clinical cutoff value is determined by resistance levels associated with treatment failure (statistical analysis of overall trial results).

"$IC_n$" refers to Inhibitory Concentration. It is the concentration of drug in the patient's blood or in vitro needed to suppress the reproduction of a disease-causing microorganism (such as HIV) by n %. Thus, "$IC_{50}$" refers to the concentration of an anti-viral agent at which virus replication is inhibited by 50% of the level observed in the absence of the drug. "Patient $IC_{50}$" refers to the drug concentration required to inhibit replication of the virus from a patient by 50% and "reference $IC_{50}$" refers to the drug concentration required to inhibit replication of a reference or wild-type virus by 50%. Similarly, "$IC_{90}$" refers to the concentration of an anti-viral agent at which 90% of virus replication is inhibited.

A "fold change" is a numeric comparison of the drug susceptibility of a patient virus and a drug-sensitive reference virus. It is the ratio of the Patient $IC_{50}$ to the drug-sensitive reference $IC_{50}$, i.e., Patient $IC_{50}$/Reference $IC_{50}$=Fold Change ("FC"). A fold change of 1.0 indicates that the patient virus exhibits the same degree of drug susceptibility as the drug-sensitive reference virus. A fold change less than 1 indicates the patient virus is more sensitive than the drug-sensitive reference virus. A fold change greater than 1 indicates the patient virus is less susceptible than the drug-sensitive reference virus. A fold change equal to or greater than the clinical cutoff value means the patient virus has a lower probability of response to that drug. A fold change less than the clinical cutoff value means the patient virus is sensitive to that drug.

"Lopinavir Fold Change" refers to the ratio of the $IC_{50}$ of lopinavir against the HIV from the patient plasma sample to the $IC_{50}$ for lopinavir against the NL4-3 (GenBank Accession No. AF324493) reference viral strain.

A virus is "sensitive" to lopinavir if it has a lopinavir fold change less than ten.

A virus is "resistant" to lopinavir if it has a lopinavir fold change of 10 or more.

A virus has an "increased likelihood of having reduced susceptibility" to an anti-viral treatment if the virus has a property, for example, a mutation, that is correlated with a reduced susceptibility to the anti-viral treatment. A property of a virus is correlated with a reduced susceptibility if a population of viruses having the property is, on average, less susceptible to the anti-viral treatment than an otherwise similar population of viruses lacking the property. Thus, the correlation between the presence of the property and; reduced susceptibility need not be absolute, nor is there a requirement that the property is necessary (i.e., that the property plays a causal role in reducing susceptibility) or sufficient (i.e., that the presence of the property alone is sufficient) for conferring reduced susceptibility.

The term "% sequence homology" is used interchangeably herein with the terms "% homology," "% sequence identity" and "% identity" and refers to the level of amino acid sequence identity between two or more peptide sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 60, 70, 80, 85, 90, 95, 98% or more sequence identity to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at http://www.ncbi.nlm.nih.gov/BLAST/. See also Altschul et al., 1990, *J. Mol. Biol.* 215:403-10 (with special reference to the published default setting, i.e., parameters w=4, t=17) and Altschul et al., 1997, *Nucleic Acids Res.,* 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Altschul, et al., 1997.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Arg (R), Asn (N), Asp (D), Glu (E), Gln (Q), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, J. Mol. Biol. 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include Arg (R), His (H) and Lys (K).

A "mutation" is a change in an amino acid sequence or in a corresponding nucleic acid sequence relative to a reference nucleic acid or protein. For embodiments of the invention comprising HIV protease, the reference protease is the protease present in NL4-3 HIV (GenBank Accession No. AF324493). Although the amino acid sequence of a peptide can be determined directly by, for example, Edman degradation or mass spectroscopy, more typically, the amino acid sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, *Methods in Enzymology* 65:499), dideoxy sequencing (Sanger et al., 1977, *Proc. Natl. Acad. Sci. USA* 74:5463) or hybridization-based approaches (see e.g., Maniatis et al., 1989, *Molecular Cloning: A Laboratory Manual,* Cold Spring Harbor Laboratory, N.Y. and Ausubel et al., 1989, *Current Protocols in Molecular Biology,* Greene Publishing Associates and Wiley Interscience, N.Y.).

A "resistance-associated mutation" ("RAM") in a virus is a mutation correlated with reduced susceptibility of the virus to anti-viral agents. A RAM can be found in several viruses, including, but not limited to a human immunodeficiency virus ("HIV"). Such mutations can be found in one or more of the viral proteins, for example, in the protease, integrase, envelope or reverse transcriptase of HIV. A RAM is defined relative to a reference strain. For embodiments of the invention comprising HIV protease, the reference protease is the protease present in NL4-3 HIV (GenBank Accession No. AF324493).

A "mutant" is a virus, gene or protein having a sequence that has one or more changes relative to a reference virus, gene or protein.

The terms "peptide," "polypeptide" and "protein" are used interchangeably throughout.

The terms "reference" and "wild-type" are used interchangeably throughout.

The terms "polynucleotide," "oligonucleotide" and "nucleic acid" are used interchangeably throughout.

The term "about" refers to numbers 10% above or 10% below the number it is modifying. In instances where the number must be an integer, for example, nucleic acid length or amino acid length, if the resulting number is not an integer, then it is rounded up or rounded down to the nearest integer greater than zero.

5.3 Resistance-Associated Mutations

The present invention provides nucleic acids and polypeptides comprising a mutation in the protease of HIV. Preferably, the HIV is human immunodeficiency virus type 1 ("HIV-1"). The HIV can also, for example, be human immunodeficiency virus type 2 ("HIV-2"). In one embodiment, the mutation is associated with reduced susceptibility to a protease inhibitor. In another embodiment, the mutation is associated with increased susceptibility to a protease inhibitor. The protease inhibitor can be any protease inhibitor known to one of skill in the art. Examples of protease inhibitors include, but are not limited to, saquinavir, ritonavir, indinavir, nelfinavir, amprenavir and lopinavir. In one embodiment, the protease inhibitor is lopinavir.

In one aspect, the present invention provides peptides, polypeptides or proteins comprising a mutation in the protease of HIV associated with either reduced or increased susceptibility to a protease inhibitor, e.g., lopinavir. In one embodiment, the invention provides a polypeptide derived from the HIV protease and comprising a mutation associated with reduced susceptibility to a protease inhibitor. In another embodiment, the polypeptide comprises more than one mutation associated with reduced susceptibility to a protease inhibitor. In another embodiment, the polypeptide comprises a mutation associated with increased susceptibility to a protease inhibitor. In another embodiment, the polypeptide comprises more than one mutation associated with increased susceptibility to a protease inhibitor. Polypeptides of the invention include peptides, polypeptides and proteins that are modified or derived from these polypeptides. In one embodiment, the polypeptide comprises post-translational modifications. In another embodiment, the polypeptide comprises one or more amino acid analogs.

In one embodiment, the polypeptide comprises one or more mutations associated with reduced susceptibility to lopinavir. Table 1 provides a list of mutations associated with reduced susceptibility to lopinavir. The amino acid or nucleic acid positions referred to throughout the document, refer to the protease amino acid or nucleic acid positions in SEQ ID NO: 1 or SEQ ID NO: 2, respectively, or to the corresponding positions in other viruses, for example, those with additions or deletions in the protease and the gene that encodes the protease relative to the sequences in SEQ ID NO: 1 or SEQ ID NO: 2.

In another embodiment, the invention provides a polypeptide derived from the HIV protease and comprising a mutation selected from a group of mutations consisting of: K20I, M46V, I50L, I54A, I54M, I54S, L63T, V82S, I84A, I84L, L33F, L33I, L33V, E34D, E34K, E34Q, K43T, G48V, I50V, K55R, Q58E, G73C, G73T, T74A, T74P, T74S, L76V, P79A, P79D, P79E, L89I and L89M. In another embodiment, the mutation is selected from the group consisting of: L33F, L33I, L33V, E34D, E34K, E34Q, K43T, G48V, I50L, I50V, K55R, Q58E, G73C, G73T, T74A, T74P, T74S, L76V, P79A, P79D, P79E, L89I and L89M. In another embodiment, the mutation is selected from the group consisting of: K20I, M46V, I54M, L63T, V82S, I84A, I84L, L33I, L33V, E34D, E34K, E34Q, I50L, I50V, G73C, T74A, T74P, L76V, P79A, P79D, P79E, L89I and L89M. In another embodiment, the mutation is selected from the group consisting of: L33I, L33V, E34D, E34K, E34Q, I50L, I50V, G73C, T74A, T74P, L76V, P79A, P79D, P79E, L89I and L89M. In another embodiment, the mutation is selected from the group consisting of: K20I, E34D, E34K, E34Q, I50L, I50V, L63T, L76V, P79A, P79D, P79E, L89I and L89M. In another embodiment, the mutation is selected from the group consisting of: E34D, E34K, E34Q, I50L, I50V, L76V, P79A, P79D, P79E, L89I and L89M.

In one embodiment, the polypeptide has the amino acid sequence of SEQ ID NO: 1, except that the sequence differs from that of SEQ ID NO: 1 in that it contains at least one mutation associated with either reduced or increased susceptibility to a protease inhibitor, e.g., lopinavir. In other embodiments, such a polypeptide includes at least 5, 10, 15, 20, 25, 30, 40, 50, 60, 70, 80, 85, 90 or 95 contiguous amino acids of SEQ ID NO: 1.

In another embodiment, such a polypeptide comprises residues 1-10 of the amino acid sequence of SEQ ID NO:1. In another embodiment, the polypeptide comprises residues 11-20 of the amino acid sequence of SEQ ID NO:1. In another embodiment, the polypeptide comprises residues 21-30 of the amino acid sequence of SEQ ID NO:1. In another embodiment, the polypeptide comprises residues 31-40 of the amino acid sequence of SEQ ID NO:1. In another embodiment, the polypeptide comprises residues 41-50 of the amino acid sequence of SEQ ID NO:1. In another embodiment, the polypeptide comprises residues 51-60 of the amino acid sequence of SEQ ID NO:1. In another embodiment, the polypeptide comprises residues 61-70 of the amino acid sequence of SEQ ID NO:1. In another embodiment, the polypeptide comprises residues 71-80 of the amino acid sequence of SEQ ID NO:1. In another embodiment, the polypeptide comprises residues 81-90 of the amino acid sequence of SEQ ID NO:1. In another embodiment, the polypeptide comprises residues 91-99 of the amino acid sequence of SEQ ID NO:1.

In another embodiment, the polypeptide is at least 70%, but less than 100%, identical to a polypeptide having the amino acid sequence of SEQ ID NO:1. In another embodiment, the polypeptide has an amino acid sequence that is greater than 80% identical to the amino acid sequence of SEQ ID NO:1. In another embodiment, the polypeptide has an amino acid sequence that is greater than 90% identical to the amino acid sequence of SEQ ID NO:1.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (% identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search that detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) that is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.,* 10:3-5; and FASTA described in Pearson and Lipman (1988) *Proc. Natl. Acad. Sci.*

85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA.

The percent identity between two sequences can be determined using techniques similar to those described above, with or without allowing gaps. In calculating percent identity, typically exact matches are counted.

In another embodiment, the present invention provides naturally-occurring or synthetically designed allelic variants of the polypeptides having an amino acid sequence of SEQ ID NO: 1. In another embodiment, the present invention provides polypeptides encoded by a nucleic acid molecule that is a naturally-occurring or synthetically designed allelic variant of a nucleic acid molecule having the nucleic acid sequence of SEQ ID NO: 2 or a complement thereof, except that the polypeptide differs from that encoded by SEQ ID NO: 2 in that it contains at least one mutation associated with either reduced or increased susceptibility to a protease inhibitor, e.g., lopinavir.

In another aspect, the present invention provides polynucleotides, oligonucleotides or nucleic acids encoding or relating to a polypeptide of the invention or a biologically active portion thereof, including, for example, nucleic acid molecules sufficient for use as hybridization probes, PCR primers or sequencing primers for identifying, analyzing, mutating or amplifying the nucleic acids of the invention.

In one embodiment, the nucleic acid encodes a polypeptide comprising a mutation in the protease of HIV associated with either reduced or increased susceptibility to a protease inhibitor, e.g., lopinavir. In one embodiment, the invention provides a nucleic acid encoding a polypeptide derived from the HIV protease and comprising one or more mutations associated with reduced susceptibility to a protease inhibitor. In another embodiment, the nucleic acid encodes a polypeptide that comprises one or more mutations associated with increased susceptibility to a protease inhibitor. Nucleic acids of the invention include nucleic acids, polynucleotides and oligonucleotides that are modified or derived from these nucleic acid sequences. In one embodiment, the nucleic acid comprises nucleic acid analogs.

In one embodiment, the nucleic acid can be the length of an HIV genome, i.e., about 9200 nucleotides. In another embodiment, the nucleic acid can be about the length of a HIV protease coding sequence, e.g., about 300 nucleotides. In other embodiments, the nucleic acid can correspond to a fragment of a HIV genome or a fragment of a HIV protease coding sequence. For example, the nucleic acid can be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 100, 110, 120, 125, 150, 175, 200, 250 or 300 nucleotides in length. Alternatively, the nucleic acid can be, for example, about 350, 375, 400, 425, 450, 475 or 500 nucleotides in length. The nucleic acid can be, for example, less than 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 100, 110, 120, 125, 150, 175, 200, 250, 300, 350, 375, 400, 425, 450, 475, 500, 525, 550, 575, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500 or 9000 nucleotides in length. In a preferred embodiment, the nucleic acid has a length and a sequence suitable for detecting a mutation described herein, for example, as a probe or a primer.

In one embodiment, the nucleic acid encodes a polypeptide that comprises one or more mutations associated with reduced susceptibility to lopinavir. Table 1 provides a list of mutations associated with reduced susceptibility to lopinavir.

In another embodiment, the invention provides a nucleic acid encoding a polypeptide derived from the HIV protease and comprising a mutation selected from a group of mutations consisting of: K20I, M46V, I54A, I54M, I54S, L63T, V82S, I84A, I84L, L33F, L33I, L33V, E34D, E34K, E34Q, K43T, G48V, I50L, I50V, K55R, Q58E, G73C, G73T, T74A, T74P, T74S, L76V, P79A, P79D, P79E, L89I and L89M. In another embodiment, the mutation is selected from the group consisting of: L33F, L33I, L33V, E34D, E34K, E34Q, K43T, G48V, I50L, I50V, K55R, Q58E, G73C, G73T, T74A, T74P, T74S, L76V, P79A, P79D, P79E, L89I and L89M. In another embodiment, the mutation is selected from the group consisting of: K20I, M46V, I54M, L63T, V82S, I84A, I84L, L33I, L33V, E34D, E34K, E34Q, I50L, I50V, G73C, T74A, T74P, L76V, P79A, P79D, P79E, L89I and L89M. In another embodiment, the mutation is selected from the group consisting of: L33I, L33V, E34D, E34K, E34Q, I50L, I50V, G73C, T74A, T74P, L76V, P79A, P79D, P79E, L89I and L89M. In another embodiment, the mutation is selected from the group consisting of: K20I, E34D, E34K, E34Q, I50L, I50V, L63T, L76V, P79A, P79D, P79E, L89I and L89M. In another embodiment, the mutation is selected from the group consisting of: E34D, E34K, E34Q, I50L, I50V, L76V, P79A, P79D, P79E, L89I and L89M.

In another embodiment, the oligonucleotide has the nucleic acid sequence of SEQ ID NO: 2, except that the sequence differs from that of SEQ ID NO: 2 in that it encodes at least one mutation associated with either reduced or increased susceptibility to a protease inhibitor, e.g., lopinavir. In other embodiments, such an oligonucleotide includes at least 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 150, 180, 210, 240, 255, 270 or 285 contiguous nucleic acids of SEQ ID NO: 2.

In another embodiment, such an oligonucleotide comprises residues 1-30 of the nucleic acid sequence of SEQ ID NO:2. In another embodiment, the oligonucleotide comprises residues 31-60 of the nucleic acid sequence of SEQ ID NO:2. In another embodiment, the oligonucleotide comprises residues 61-90 of the nucleic acid sequence of SEQ ID NO:2. In another embodiment, the oligonucleotide comprises residues 91-120 of the nucleic acid sequence of SEQ ID NO:2. In another embodiment, the oligonucleotide comprises residues 121-150 of the nucleic acid sequence of SEQ ID NO:2. In another embodiment, the oligonucleotide comprises residues 151-180 of the nucleic acid sequence of SEQ ID NO:2. In another embodiment, the oligonucleotide comprises residues 181-210 of the nucleic acid sequence of SEQ ID NO:2. In another embodiment, the oligonucleotide comprises residues 211-240 of the nucleic acid sequence of SEQ ID NO:2. In another embodiment, the oligonucleotide comprises residues 241-270 of the nucleic acid sequence of SEQ ID NO:2. In another embodiment, the oligonucleotide comprises residues 271-297 of the nucleic acid sequence of SEQ ID NO:2.

In another embodiment, the oligonucleotide is at least 60%, but less than 100%, identical to an oligonucleotide having the nucleic acid sequence of SEQ ID NO:2. In another embodiment, the oligonucleotide has an nucleic acid sequence that is greater than 70% identical to the nucleic acid sequence of SEQ ID NO:2. In another embodiment, the oligonucleotide has an nucleic acid sequence that is greater than 80% identical to the nucleic acid sequence of SEQ ID NO:2. In another embodiment, the oligonucleotide has an nucleic acid sequence that is greater than 90% identical to the nucleic acid sequence of SEQ ID NO:2. The percent identity of two nucleic acid sequences can be determined as described above.

In addition to the nucleotide sequence of SEQ ID NO: 2, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. Natural allelic variations can typically result in 1-5% variance in the nucleotide sequence of a given gene. Any and all such nucleotide variations and resulting amino acid variations or polymorphisms that are the result of natural allelic variation and that do not alter the functional activity are intended to be within the scope of the invention.

In another embodiment, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full length polypeptide of the invention for example, a fragment that can be used as a probe or primer or a fragment encoding a biologically active portion of a polypeptide of the invention. The probe can comprise a labeled group attached thereto, e.g., a radioisotope, a fluorescent compound, an enzyme, or an enzyme co-factor. In various embodiments, the nucleic acid molecules of the invention can be modified at the base moiety, sugar moiety or phosphate backbone.

5.4 Finding Drug Resistance-Associated Viral Mutations

In another aspect, the present invention provides methods for finding resistance-associated mutation in a virus or a derivative of the virus.

5.4.1 The Virus and Viral Samples

A resistance-associated mutation ("RAM") according to the present invention can be present in any type of virus, for example, any virus found in animals. In one embodiment of the invention, the virus includes viruses known to infect mammals, including dogs, cats, horses, sheep, cows etc. In a preferred embodiment, the virus is known to infect primates. In an even more preferred embodiment the virus is known to infect humans. Examples of human viruses include, but are not limited to, human immunodeficiency virus ("HIV"), herpes simplex virus, cytomegalovirus virus, varicella zoster virus, other human herpes viruses, influenza A virus, respiratory syncytial virus, hepatitis A, B and C viruses, rhinovirus, and human papilloma virus. In one embodiment of the invention, the virus is HIV. Preferably, the virus is human immunodeficiency virus type 1 ("HIV-1"). The HIV can also, for example, be human immunodeficiency virus type 2 ("HIV-2"). The foregoing are representative of certain viruses for which there is presently available anti-viral chemotherapy and represent the viral families retroviridae, herpesviridae, orthomyxoviridae, paramxyxovirus, picornavirus, flavivirus, pneumovirus and hepadnaviridae. This invention can be used with other viral infections due to other viruses within these families as well as viral infections arising from viruses in other viral families for which there is or there is not a currently available therapy.

A RAM according to the present invention can be found in a viral sample obtained by any means known in the art for obtaining viral samples. Such methods include, but are not limited to,: obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus and samples of other bodily fluids. In one embodiment, the sample is a blood, serum or plasma sample.

In another embodiment, a RAM according to the present invention is present in a virus that can be obtained from a culture. In some embodiments, the culture can be obtained from a laboratory. In other embodiments, the culture can be obtained from a collection, for example, the American Type Culture Collection.

In certain embodiments, a RAM according to the present invention is present in a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of the selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes of interest can be incorporated into a vector. See, e.g., U.S. Pat. Nos. 5,837,464 and 6,242,187 and PCT publication, WO 99/67427, each of which is incorporated herein by reference. In a preferred embodiment, the genes can be those that encode for a protease or reverse transcriptase.

In another embodiment, the intact virus need not be used. Instead, a part of the virus incorporated into a vector can be used. Preferably that part of the virus is used that is targeted by an anti-viral drug.

In another embodiment, a RAM according to the present invention is present in a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an anti-viral treatment. Any known anti-viral treatment can be used as the selective pressure. In one embodiment, the virus is HIV and the selective pressure is a protease inhibitor. In another embodiment, the virus is HIV-1 and the selective pressure is a protease inhibitor. Any protease inhibitor can be used to apply the selective pressure. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir. In another embodiment, the protease inhibitor is lopinavir. By treating HIV cultured in vitro with a protease inhibitor, e.g., lopinavir, one can select for mutant strains of HIV that have an increased resistance to amprenavir. The stringency of the selective pressure can be manipulated to increase or decrease the survival of viruses not having the selected-for characteristic.

In another aspect, a RAM according to the present invention is made by mutagenizing a virus, a viral genome, or a part of a viral genome. Any method of mutagenesis known in the art can be used for this purpose. In one embodiment, the mutagenesis is essentially random. In another embodiment, the essentially random mutagenesis is performed by exposing the virus, viral genome or part of the viral genome to a mutagenic treatment. In another embodiment, a gene that encodes a viral protein that is the target of an anti-viral therapy is mutagenized. Examples of essentially random mutagenic treatments include, for example, exposure to mutagenic substances (e.g., ethidium bromide, ethylmethanesulphonate, ethyl nitroso urea (ENU) etc.) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., 1979, *Proc. Nat. Acad. Sci. USA* 76:5918-5922; Russell, W., 1982, Environmental Mutagens and Carcinogens: Proceedings of the Third International Conference on Environmental Mutagens. One of skill in the art will appreciate that while each of these methods of mutagenesis is essentially random, at a molecular level, each has its own preferred targets.

In another aspect, a mutation that might affect the sensitivity of a virus to an anti-viral therapy is made using site-directed mutagenesis. Any method of site-directed mutagenesis known in the art can be used (see e.g., Maniatis et al., 1989, *Molecular Cloning: A Laboratory Manual,* Cold Spring Harbor Laboratory, N.Y. and Ausubel et al., 1989, *Current Protocols in Molecular Biology,* Greene Publishing Associates and Wiley Interscience, N.Y.). The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an anti-viral therapy, e.g., the gene encoding the HIV protease. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains having decreased susceptibility to the anti-viral treatment. In another embodiment, the mutagenized nucleotides encode amino acid residues that are adjacent to or near in the primary sequence of the protein residues known or suspected to interact with an anti-viral compound or known or suspected to be mutated in viral strains having decreased susceptibility to an anti-viral treatment. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having decreased susceptibility to an anti-viral treatment. In another embodiment, the mutagenized nucleotides encode amino acid residues in or near the active site of a protein that is known or suspected to bind to an anti-viral compound. See, e.g., Sarkar and Sommer, 1990, *Biotechniques,* 8:404-407.

5.4.2 Detecting the Presence or Absence of Mutations in a Virus

The presence or absence of a RAM according to the present invention in a virus can be detected by any means known in the art for detecting a mutation. The mutation can be detected in the viral gene that encodes a particular protein, or in the protein itself, i.e., in the amino acid sequence of the protein.

In one embodiment, the mutation is in the viral genome. Such a mutation can be in, for example, a gene encoding a viral protein, in a cis or trans acting regulatory sequence of a gene encoding a viral protein, an intergenic sequence, or an intron sequence. The mutation can affect any aspect of the structure, function, replication or environment of the virus that changes its susceptibility to an anti-viral treatment. In one embodiment, the mutation is in a gene encoding a viral protein that is the target of an anti-viral treatment.

A mutation within a viral gene can be detected by utilizing a number of techniques. Viral DNA or RNA can be used as the starting point for such assay techniques, and may be isolated according to standard procedures which are well known to those of skill in the art.

Viral DNA or RNA may be used in hybridization or amplification assays to detect abnormalities involving gene structure, including point mutations, insertions, deletions and genomic rearrangements. Such assays may include, but are not limited to, Southern analyses (Southern, 1975, *J. Mol. Biol.* 98:503-517), single stranded conformational polymorphism analyses (SSCP) (Orita et al., 1989, *Proc. Natl. Acad. Sci. USA* 86:2766-2770), and PCR analyses (U.S. Pat. Nos. 4,683,202; 4,683,195; 4,800,159; and 4,965,188; PCR Strategies, 1995 Innis et al. (eds.), Academic Press, Inc.).

Such diagnostic methods for the detection of a gene-specific mutation can involve for example, contacting and incubating the viral nucleic acids with one or more labeled nucleic acid reagents including recombinant DNA molecules, cloned genes or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

Alternative diagnostic methods for the detection of gene specific nucleic acid molecules may involve their amplification, e.g., by PCR (U.S. Pat. Nos. 4,683,202; 4,683,195; 4,800,159; and 4,965,188; PCR Strategies, 1995 Innis et al. (eds.), Academic Press, Inc.), followed by the detection of the amplified molecules using techniques well known to those of skill in the art. The resulting amplified sequences can be compared to those which would be expected if the nucleic acid being amplified contained only normal copies of the respective gene in order to determine whether a gene mutation exists.

Additionally, the nucleic acid can be sequenced by any sequencing method known in the art. For example, the viral DNA can be sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499. See also the techniques described in Maniatis et al., 1989, *Molecular Cloning: A Laboratory Manual*, Cold Spring Harbor Laboratory, N.Y. and Ausubel et al., 1989, *Current Protocols in Molecular Biology*, Greene Publishing Associates and Wiley Interscience, N.Y.

Antibodies directed against the viral gene products, i.e., viral proteins or viral peptide fragments can also be used to detect mutations in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

5.5 Measuring Phenotypic Susceptibility of a Mutant Virus

Any method known in the art can be used to determine the phenotypic susceptibility of a mutant virus or population of viruses to an anti-viral therapy. See e.g., U.S. Pat. Nos. 5,837,464 and 6,242,187, incorporated herein by reference in their entirities. In some embodiments a phenotypic analysis is performed, i.e., the susceptibility of the virus to a given anti-viral agent can be assayed with respect to the susceptibility of a reference virus without the mutations. This is a direct, quantitative measure of drug susceptibility and can be performed by any method known in the art to determine the susceptibility of a virus to an anti-viral agent. An example of such methods includes, but is not limited to, determining the fold change in $IC_{50}$ values with respect to a reference virus. Phenotypic testing measures the ability of a specific viral strain to grow in vitro in the presence of a drug inhibitor. A virus is less susceptible to a particular drug when more of the drug is required to inhibit viral activity, versus the amount of drug required to inhibit the reference virus.

In one embodiment, phenotypic analysis is performed and used to calculate the $IC_{50}$ or $IC_{90}$ of a drug for a viral strain. The results of the analysis can also be presented as fold-change in $IC_{50}$ or $IC_{90}$ for each viral strain as compared with a drug-susceptible control strain or a prior viral strain from the same patient. Because the virus is directly exposed to each of the available anti-viral medications, results can be directly linked to treatment response. For example, if the patient virus shows resistance to a particular drug, that drug is avoided or omitted from the patient's treatment regimen, allowing the physician to design a treatment plan that is more likely to be effective for a longer period of time.

In another embodiment, the phenotypic analysis is performed using recombinant virus assays ("RVAs"). RVAs use virus stocks generated by homologous recombination between viral vectors and viral gene sequences, amplified from the patient virus. In some, embodiments, the viral vector is a HIV vector and the viral gene sequences can be protease and reverse transcriptase sequences.

In one embodiment, the phenotypic analysis is performed using PHENOSENSE™ (ViroLogic Inc., South San Francisco, Calif.). See Petropoulos et al., 2000, *Antimicrob. Agents Chemother.* 44:920-928; U.S. Pat. Nos. 5,837,464 and 6,242,187. PHENOSENSE™ is a phenotypic assay that achieves the benefits of phenotypic testing and overcomes the drawbacks of previous assays. Because the assay has been automated, PHENOSENSE™ offers higher throughput under controlled conditions. The result is an assay that accurately defines the susceptibility profile of a patient's HIV isolates to all currently available antiretroviral drugs, and delivers results directly to the physician within about 10 to about 15 days of sample receipt. PHENOSENSE™ is accurate and can obtain results with only one round of viral replication, thereby avoiding selection of subpopulations of virus. The results are quantitative, measuring varying degrees of drug susceptibility, and sensitive—the test can be performed on blood specimens with a viral load of about 500 copies/mL and can detect minority populations of some drug-resistant virus at concentrations of 10% or less of total viral population. Furthermore, the results are reproducible and can vary by less than about 1.4-2.5 fold, depending on the drug, in about 95% of the assays performed.

PHENOSENSE™ can be used with nucleic acids from amplified viral gene sequences. As discussed in Section 5.4.1, the sample containing the virus may be a sample from a human or an animal infected with the virus or a sample from a culture of viral cells. In one embodiment, the viral sample comprises a genetically modified laboratory strain.

A resistance test vector ("RTV") can then be constructed by incorporating the amplified viral gene sequences into a replication defective viral vector by using any method known in the art of incorporating gene sequences into a vector. In one embodiment, restrictions enzymes and conventional cloning methods are used. See Maniatis et al., 1989, *Molecular Cloning: A Laboratory Manual*, Cold Spring Harbor Laboratory, N.Y. and Ausubel et al., 1989, *Current Protocols in Molecular Biology*, Greene Publishing Associates and Wiley Interscience, N.Y. In some embodiments, ApaI and PinAI restriction enzymes are used. Preferably, the replication defective viral vector is the indicator gene viral vector ("IGVV"). In some embodiments, the viral vector contains a means for detecting replication of the RTV. Preferably, the viral vector contains a luciferase expression cassette.

The assay can be performed by first co-transfecting host cells with RTV DNA and a plasmid that expresses the envelope proteins of another retrovirus, for example, amphotropic murine leukemia virus (MLV). Following transfection, virus particles can be harvested and used to infect fresh target cells. The completion of a single round of viral replication can be detected by the means for detecting replication contained in the vector. In one embodiment, the completion of a single round of viral replication results in the production of luciferase. Serial concentrations of anti-viral agents can be added at either the transfection step or the infection step.

Susceptibility to the anti-viral agent can be measured by comparing the replication of the vector in the presence and absence of the anti-viral agent. For example, susceptibility to the anti-viral agent can be measured by comparing the luciferase activity in the presence and absence of the anti-viral agent. Susceptible viruses would produce low levels of luciferase activity in the presence of anti-viral agents, whereas viruses with reduced susceptibility would produce higher levels of luciferase activity.

In one embodiment, PHENOSENSE™ is used in evaluating the phenotypic susceptibility of HIV-1 to anti-viral drugs. Preferably, the anti-viral drug is a protease inhibitor. More preferably, it is lopinavir. In some embodiments, the reference viral strain is HIV strain NL4-3 or HXB-2.

In one embodiment, viral nucleic acid, for example, HIV-1 RNA can be extracted from plasma samples, and a fragment of, or entire viral genes could be amplified by methods such as, but not limited to PCR. See, e.g., Hertogs et al., 1998, *Antimicrob Agents Chemother* 42(2):269-76. In one example, a 2.2-kb fragment containing the entire HIV-1 PR- and RT-coding sequence can be amplified by nested reverse transcription-PCR. The pool of amplified nucleic acid, for example, the PR-RT-coding sequences, can then be cotransfected into a host cell such as CD4+ T lymphocytes (MT4) with the pGEMT3deltaPRT plasmid from which most of the PR (codons 10 to 99) and RT (codons 1 to 482) sequences are deleted. Homologous recombination leads to the generation of chimeric viruses containing viral coding sequences, such as the PR- and RT-coding sequences derived from HIV-1 RNA in plasma. The susceptibilities of the chimeric viruses to all currently available anti-viral agents targeting the products of the transfected genes (proRT and/or PR inhibitors, for example), can be determined by any cell viability assay known in the art. For example, an MT4 cell-3-(4,5-dimethylthiazol-2-yl)-2,5-diphenyltetrazolium bromide-based cell viability assay can be used in an automated system that allows high sample throughput. The profile of resistance to all the anti-viral agents, such as the RT and PR inhibitors can be displayed graphically in a single PR-RT-Antivirogram.

Other assays for evaluating the phenotypic susceptibility of a virus to anti-viral drugs known to one of skill in the art can be used. See, e.g., Shi and Mellors, 1997, *Antimicrob Agents Chemother.* 41(12):2781-85; Gervaix et al., 1997, *Proc Natl Acad Sci U.S.A.* 94(9):4653-8, incorporated herein by reference in their entirities.

In another embodiment, the susceptibility of a virus to treatment with an anti-viral treatment is determined by assaying the activity of the target of the anti-viral treatment in the presence of the anti-viral treatment. In one embodiment, the virus is HIV, the anti-viral treatment is a protease inhibitor, and the target of the anti-viral treatment is the HIV protease. See, e.g., U.S. Pat. Nos. 5,436,131, 6,103,462, incorporated herein by reference in their entirities.

5.6 Correlating Phenotypic and Genotypic Susceptibility

Any method known in the art can be used to determine whether a mutation is correlated with a decrease in susceptibility of a virus to an anti-viral treatment and thus is a RAM according to the present invention. In one embodiment, P values are used to determine the statistical significance of the correlation, such that the smaller the P value, the more significant the measurement. Preferably the P values will be less than 0.05. More preferably, P values will be less than 0.01. P values can be calculated by any means known to one of skill in the art. In one embodiment, P values are calculated using Fisher's Exact Test. See, e.g., David Freedman, Robert Pisani & Roger Purves, 1980, STATISTCS, W. W. Norton, New York.

In one embodiment, numbers of samples with the mutation being analyzed that have an $IC_{50}$ fold change below or above 10-fold are compared to numbers of samples without the mutation. A 2×2 table can be constructed and the P value can be calculated using Fisher's Exact Test (see Example 5). P values smaller than 0.05 or 0.01 can be classified as statistically significant.

5.7 Determining Susceptibility to the Anti-Viral Treatment

In another aspect, the present invention provides a method for determining a virus' susceptibility to anti-viral treatment. Resistance-associated mutations (RAMs) can be identified and correlated with reduced susceptibility of a virus to an anti-viral treatment as described in Sections 5.3-5.6 above. The presence of a RAM in a virus can be detected by any means known in the art, e.g., as discussed in Section 5.4.2 above. The presence of a RAM in the virus can indicate that the virus has an increased likelihood of having reduced susceptibility for the anti-viral treatment. In one embodiment, the virus is human immunodeficiency virus (HIV). In another embodiment, the virus is human immunodeficiency virus type-1 (HIV-1). In another embodiment, the anti-viral treatment is a protease inhibitor. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir. In another embodiment, the protease inhibitor is lopinavir.

In another embodiment, the invention provides a method for determining whether a HIV has an increased likelihood of having a reduced susceptibility to treatment with a protease inhibitor, comprising detecting in the protease of said HIV or in a nucleic acid of said HIV that encodes the protease, the presence or absence of a mutation associated with reduced susceptibility to treatment with said protease inhibitor at amino acid position 20, 33, 34, 43, 46, 48, 50, 54, 55, 58, 63, 66, 73, 74, 76, 79, 82, 84 or 89 of the amino acid sequence of said protease, wherein the presence of said mutation indicates that the HIV has an increased likelihood of having reduced susceptibility to treatment with the protease inhibitor compared to a HIV without said mutation, e.g., a wild type or reference HIV, with the proviso that said mutation is not K20M, K20R, M46I, M46L, I54L, I54T, I54V, L63P, V82A, V82F, V82T or I84V. In one embodiment, the mutation is detected in the protease of said HIV. In another embodiment, the mutation is detected in a nucleic acid of said HIV that encodes the protease.

In another embodiment, the mutation associated with reduced susceptibility to treatment with said protease inhibitor is at amino acid position 20, 33, 34, 46, 50, 54, 63, 66, 73, 74, 76, 79, 82, 84 or 89 of the amino acid sequence of said protease, with the proviso that said mutation is not K20M, K20R, L33F, L33M, K43T, M46I, M46L, I50V, I54A, I54L, I54M, I54S, I54T, I54V, L63P, G73A, G73S, G73T, T74S, V82A, V82F, V82I, V82S, V82T or I84V.

In another embodiment, the mutation associated with reduced susceptibility to treatment with said protease inhibitor is at amino acid position 10, 11, 32, 47, 53, 71 or 95 of the amino acid sequence of said protease, with the proviso that said mutation is not V32I or I47V. In one embodiment, the mutation associated with reduced susceptibility to treatment with said protease inhibitor is selected from the group consisting of: L10F, F53L and A71L.

In another embodiment, the mutation associated with reduced susceptibility to treatment with said protease inhibitor is selected from the group consisting of: K20I, M46V, I50L, I54A, I54M, I54S, L63T, V82S, I84A, I84L, L33F, L33I, L33V, E34D, E34K, E34Q, K43T, G48V, I50L, I50V, K55R, Q58E, G73C, G73T, T74A, T74P, T74S, L76V, P79A, P79D, P79E, L89I and L89M. In another embodiment, the mutation is selected from the group consisting of: K20I, M46V, I50L, L63T, I84A, I84L, L33I, L33V, E34D, E34K, E34Q, I50V, I54M, G73C, T74A, T74P, L76V, P79A, P79D, P79E, L89I and L89. In another embodiment, the mutation is selected from the group consisting of: K20I, M46V, I50L, L63T, I84A, I84L, L33I, L33V, E34D, E34K, E34Q, G73C, T74A, T74P, L76V, P79A, P79D, P79E, L89I and L89M.

In another aspect, the invention provides a method for determining whether a HIV has an increased likelihood of having a reduced susceptibility to treatment with a first protease inhibitor, comprising detecting in the protease of said HIV the presence or absence of a mutation associated with reduced susceptibility to treatment with a second protease inhibitor, wherein the presence of said mutation indicates that the HIV has an increased likelihood of having reduced susceptibility to treatment with said first protease inhibitor. In one embodiment, the first protease inhibitor is lopinavir or amprenavir. In another embodiment, the second protease inhibitor is lopinavir or amprenavir. In another embodiment, the mutations in the protease are at amino acid position 11, 32, 33, 34, 43, 46, 47, 48, 50, 54, 58, 71, 76, 79, 82, 84 or 95 of the amino acid sequence of said protease, with the proviso that said mutation is not V32I, M46I, M46L, I47V, I50V, I54L, I54M, V82A, or I84V.

In another embodiment, the invention provides a method of determining whether an individual infected with HIV has an increased likelihood of having a reduced susceptibility to treatment with a first protease inhibitor, comprising detecting, in a sample from said individual, the presence or absence of a mutation associated with reduced susceptibility to treatment with a second protease inhibitor at amino acid position 11, 32, 33, 34, 43, 46, 47, 48, 50, 54, 58, 71, 76, 79, 82, 84 or 95 of the amino acid sequence of the protease of the HIV, wherein the presence of said mutation indicates that the individual has an increased likelihood of having reduced susceptibility to treatment with said first protease inhibitor, with the proviso that said mutation is not V32I, M46I, M46L, I47V, I50V, I54L, I54M, V82A, or I84V. In one embodiment, the first protease inhibitor is lopinavir or amprenavir. In another embodiment, the second protease inhibitor is lopinavir or amprenavir. In another embodiment, the mutations in the protease are at amino acid position 11, 32, 33, 34, 43, 46, 47, 48, 50, 54, 58, 71, 76, 79, 82, 84 or 95 of the amino acid sequence of said protease, with the proviso that said mutation is not V32I, M46I, M46L, I47V, I50V, I54L, I54M, V82A, or I84V.

In another aspect, the present invention provides a method for determining the susceptibility of an individual infected with a virus to anti-viral treatment. Resistance-associated mutations (RAMs) can be identified and correlated with reduced susceptibility of a virus to an anti-viral treatment as described in Sections 5.3-5.6 above. The presence of a RAM in a virus present in a sample from the individual can be detected by any means known in the art, e.g., as discussed in Section 5.4.2 above. The presence of a RAM in the virus can indicate that the individual has an increased likelihood of having reduced susceptibility for the anti-viral treatment. In one embodiment, the virus is HIV. In another embodiment, the virus is HIV-1. In another embodiment, the anti-viral treatment is a protease inhibitor. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir. In another embodiment, the protease inhibitor is lopinavir.

In another embodiment, the invention provides a method for determining whether an individual infected with HIV has an increased likelihood of having a reduced susceptibility to treatment with a protease inhibitor, comprising detecting, in a sample from said individual, the presence or absence of a mutation associated with reduced susceptibility to treatment with said protease inhibitor at amino acid position 20, 33, 34, 43, 46, 48, 50, 54, 55, 58, 63, 66, 73, 74, 76, 79, 82, 84 or 89 of the amino acid sequence of the protease of the HIV, wherein the presence of said mutation indicates that the individual has an increased likelihood of having reduced susceptibility to treatment with the protease inhibitor compared to an individual infected with a HIV without said mutation, e.g., a wild type or reference HIV, with the proviso that said mutation is not K20M, K20R, M46I, M46L, I54L, I54T, I54V, L63P, V82A, V82F, V82T or I84V. In one embodiment, the mutation is detected in the protease of said HIV. In another embodiment, the mutation is detected in a nucleic acid of said HIV that encodes the protease.

In another embodiment, the invention provides a method for determining the effectiveness of protease inhibitor treatment of an individual infected with a HIV, comprising detecting, in a sample from said individual, the presence or absence of a mutation associated with reduced susceptibility to treatment with said protease inhibitor at amino acid position 20, 33, 34, 46, 50, 54, 63, 66, 73, 74, 76, 79, 82, 84 or 89 of the amino acid sequence of the protease of the HIV, wherein the presence of said mutation indicates that the individual has a reduced susceptibility to treatment with said protease inhibitor, with the proviso that said mutation is not K20M, K20R, L33F, L33M, K43T, M46I, M46L, I50V, I54A, I54L, I54M, I54S, I54T, I54V, L63P, G73A, G73S, G73T, T74S, V82A, V82F, V82I, V82S, V82T or I84V.

In another embodiment, the mutation associated with reduced susceptibility to treatment with said protease inhibitor is at amino acid position 10, 11, 32, 47, 53, 71 or 95 of the amino acid sequence of the protease of the HIV, with the proviso that said mutation is not V32I or I47V. In one embodiment, the mutation associated with reduced susceptibility to treatment with said protease inhibitor is selected from the group consisting of: L10F, F53L and A71L.

In another embodiment, the mutation associated with reduced susceptibility to treatment with said protease inhibitor is selected from the group consisting of: K20I, M46V, I50L, I54A, I54M, I54S, L63T, V82S, I84A, I84L, L33F, L33I, L33V, E34D, E34K, K43T, G48V, I50L, I50V, K55R, Q58E, G73C, G73T, T74A, T74P, T74S, L76V, P79A, P79D, P79E, L89I and L89M. In another embodiment, the mutation is selected from the group consisting of: K20I, M46V, I50L, L63T, I84A, I84L, L33I, L33V, E34D, E34K, E34Q, I50V, I54M, G73C, T74A, T74P, L76V, P79A, P79D, P79E, L89I and L89M. In another embodiment, the mutation is selected from the group consisting of: K20I, M46V, I50L, L63T, I84A, I84L, L33I, L33V, E34D, E34K, E34Q, G73C, T74A, T74P, L76V, P79A, P79D, P79E, L89I and L89M.

5.8 Constructing an Algorithm

In one aspect, the present invention provides a method of constructing an algorithm that correlates genotypic data about a virus with phenotypic data about the virus. In one embodiment, the phenotypic data relate to the susceptibility of the virus to an anti-viral treatment. In another embodiment, the anti-viral treatment is an anti-viral compound. In another embodiment, the anti-viral compound is a protease inhibitor. In another embodiment, the protease inhibitor is lopinavir.

In one embodiment, the method of constructing the algorithm comprises creating a rule or rules that correlate genotypic data about a set of viruses with phenotypic data about the set of viruses.

In one embodiment, a training data set comprising genotypic and phenotypic data about each virus in a set of viruses is assembled. Any method known in the art can be used to collect genotypic data about a virus. Examples of methods of collecting such data are provided above. Any method known in the art can be used for collecting phenotypic data about a virus. Examples of such methods are provided above. In some embodiments, the training data set comprises one or more RAMs as described above. In one embodiment, each genotypic datum is the sequence of all or part of a viral protein of a virus in the set of viruses. In another embodiment, each genotypic datum in the training data set is a single amino acid change in a protein encoded by the virus, relative to a reference protein in the reference virus. In other embodiments, the genotype comprises two, three, four, five, six or more amino acid changes in the viral protein. In another embodiment, the virus is HIV, and the protein is HIV protease. In one embodiment, the virus is HIV-1. In another embodiment, the reference protein is the protease from NL4-3 HIV.

In one embodiment, each phenotypic datum in the training data set is the susceptibility to an anti-viral treatment of a virus in the set of viruses. In one embodiment, the anti-viral treatment is an anti-viral compound. In another embodiment, the anti-viral compound is a protease inhibitor. In another embodiment, the protease inhibitor is lopinavir. In one embodiment, the susceptibility is measured as a change in the susceptibility of the virus relative to a reference virus. In another embodiment, the susceptibility is measured as a change in the $IC_{50}$ of the virus relative to a reference virus. In another embodiment, the change in $IC_{50}$ is represented as the fold-change in $IC_{50}$. In one embodiment the virus is HIV. In another embodiment, the virus is HIV-1. In another embodiment, the reference HIV is NL4-3 HIV.

Figure 1:
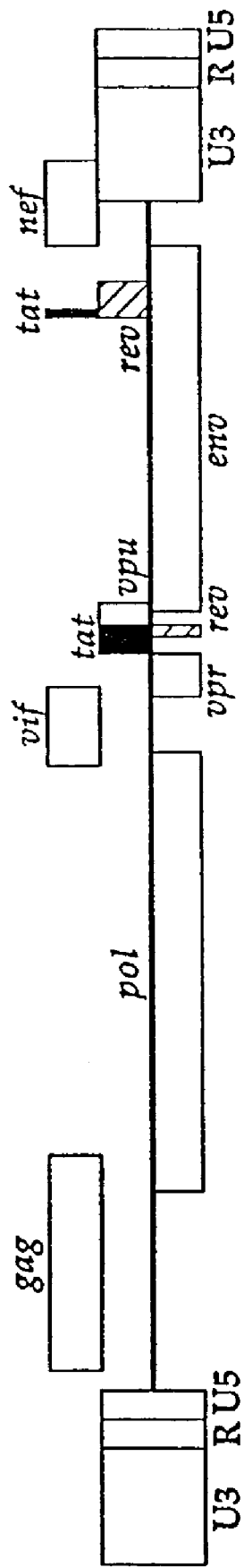
Figure 2:
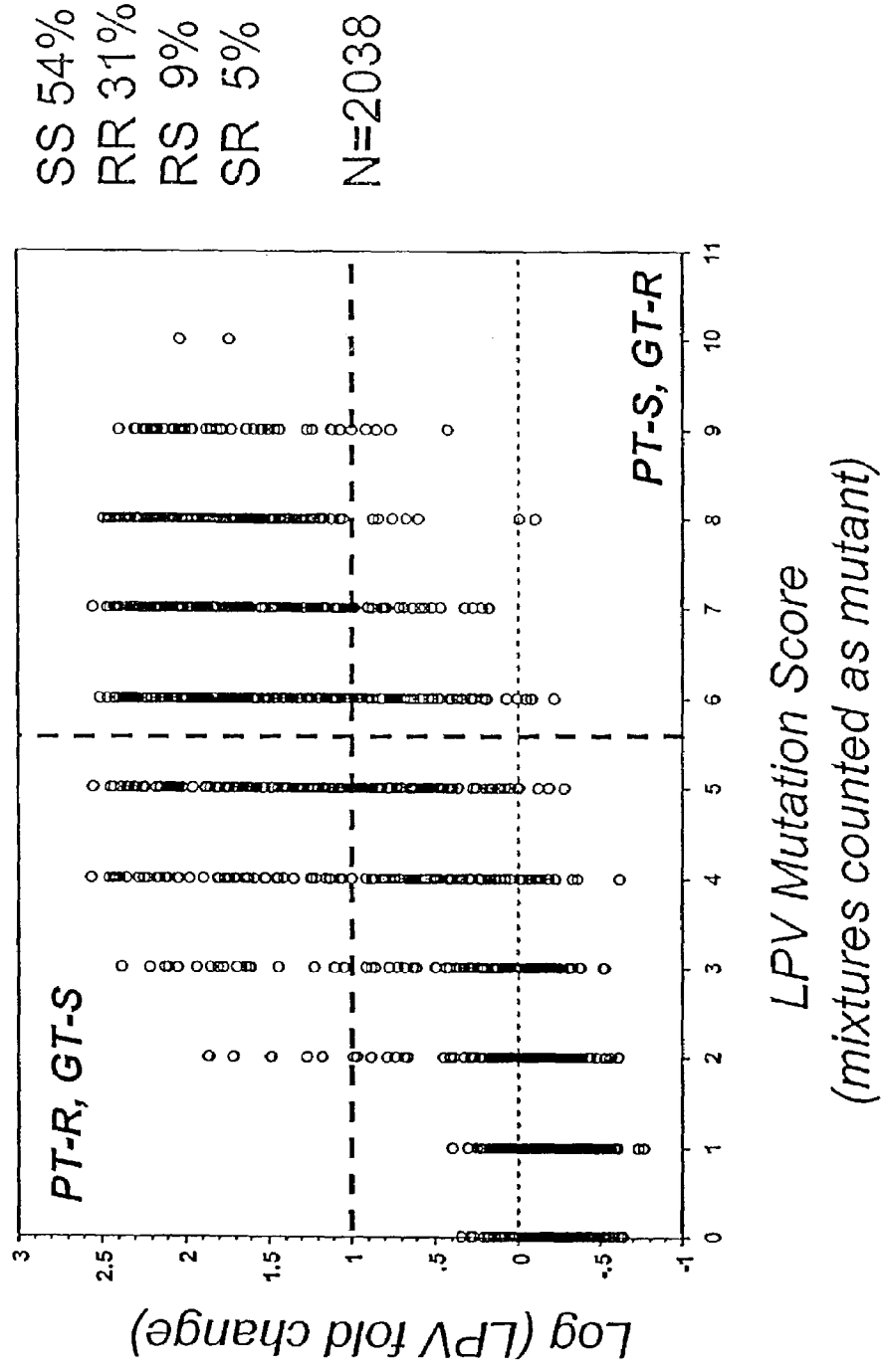
Figure 7:
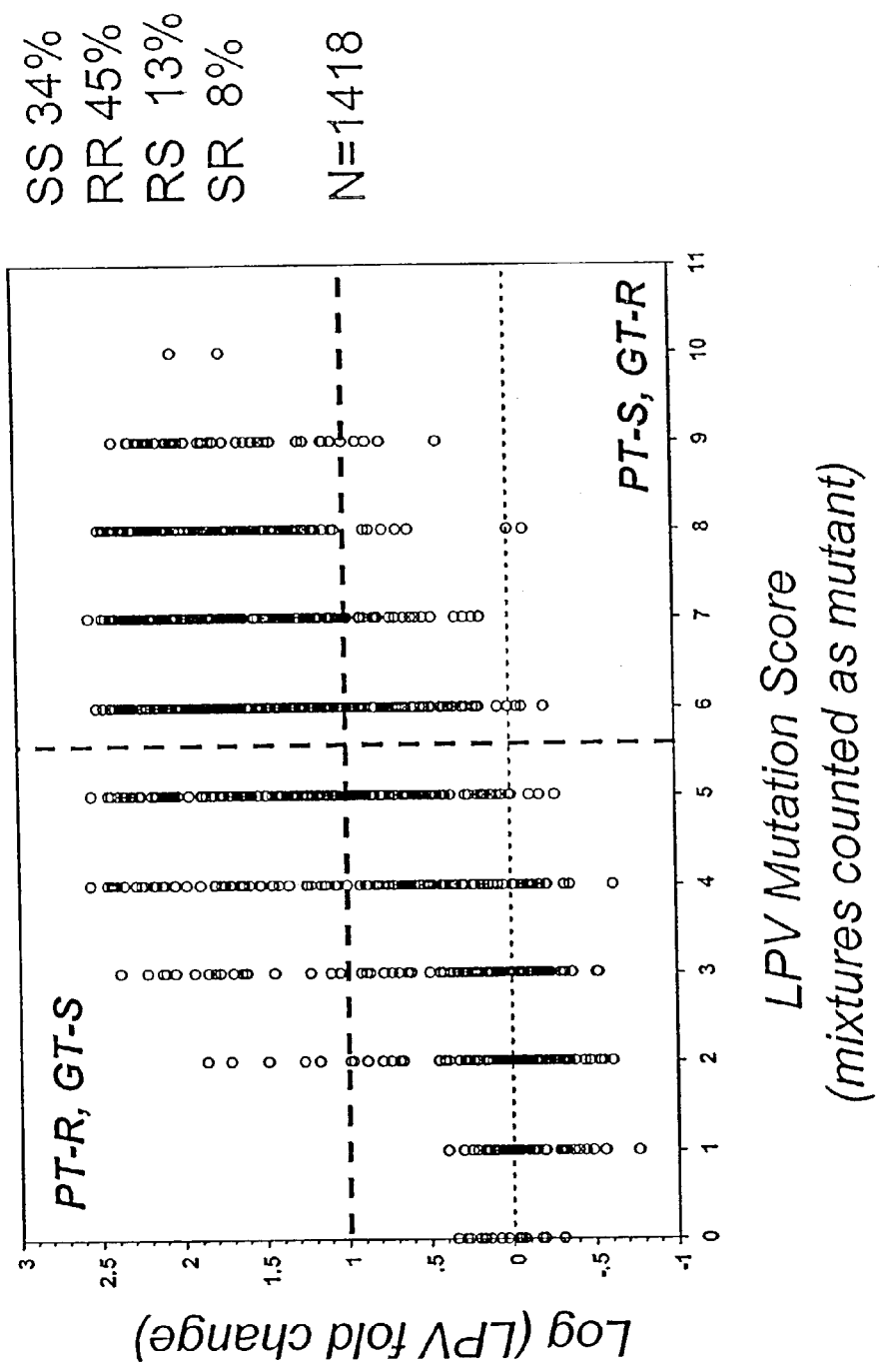
FIG. 7 is a scatter plot that shows the susceptibility to lopinavir (Log lopinavir fold change) of HIV samples as a function of the number of the resistance-associated mutations in the protease after the removal of samples without any primary mutations associated with protease inhibitors and without an $IC_{50}$ fold change ("FC") greater than two for any protease inhibitor.

The genotypic and phenotypic data in the training data set can be represented or organized in any way known in the art. In one embodiment, the data are displayed in the form of a graph, for example, as shown in FIGS. 2 and 7. In this type of representation, the y-axis represents the fold change in $IC_{50}$ of a virus in the data set relative to a reference virus. Each point on the graph corresponds to one virus in the data set. The x-axis represents the number of mutations that a virus in the data set has. The position of the point indicates both the number of mutations and the fold change in anti-viral therapy treatment that the virus has, both measured relative to a reference strain. In another embodiment, the genotypic and phenotypic data in the training data set are displayed in the form of a chart, for example, as shown in FIG. 2.

In one aspect, an algorithm is formulated that correlates the genotypic data with the phenotypic data in the training data set. In one embodiment, a phenotypic cutoff point is defined. In another embodiment, the phenotype is susceptibility to an anti-viral treatment. In another embodiment, the phenotype is change in sensitivity to an anti-viral treatment relative to a reference virus, and the cutoff point is the value above which a virus or population of viruses is defined as phenotypically resistant ("PT-R") to the anti-viral therapy and below which a virus or population of viruses is defined as phenotypically sensitive ("PT-S") to the anti-viral therapy. In other embodiments, the cutoff point is 2-fold, 5-fold, 10-fold, 15-fold, 20-fold, 30-fold, 40-fold, 50-fold or 100-fold greater than the $IC_{50}$ of a reference virus. In another embodiment, the phenotypic cutoff point is the clinical cutoff value as defined above. In another embodiment, the virus is HIV and the anti-viral therapy is treatment with a protease inhibitor. In another embodiment, the protease inhibitor is lopinavir.

In another embodiment, the phenotypic cutoff point is used to define a genotypic cutoff point. In one embodiment this is done by correlating the number of mutations in a virus of the training data set with the phenotypic susceptibility of the virus. This can be done, for example, using a graph similar to the one in FIG. 2, as discussed above. A genotypic cutoff point is selected such that most viruses having more than that number of mutations in the data set are phenotypically resistant ("PT-R"), and most viruses having fewer than that number of mutations are phenotypically sensitive ("PT-S"). By definition, a virus in the training data set with number of mutations equal to, or more than the genotypic cutoff is genotypically resistant ("GT-R") to the anti-viral treatment, and a virus in the training data set with fewer than the genotypic cutoff number of mutations is genotypically sensitive ("GT-S") to the anti-viral treatment. Thus, in one embodiment, a genotypic cutoff point is selected that produces the greatest percentage of viruses in the training data set that are either phenotypically resistant and genotypically resistant ("PT-R, GT-R"), or phenotypically sensitive and genotypically sensitive ("PT-S, GT-S").

While this simple algorithm can provide a useful approximation of the relationship between the genotypic and phenotypic data in the training data set, in most cases there will be a significant number of strains that are genotypically sensitive but phenotypically resistant ("GT-S, PT-R"), or genotypically resistant but phenotypically sensitive ("GT-R, PT-S"), as shown in FIGS. 2 and 7. These discordant results are a measure of the inaccuracy of the algorithm. Thus, in some embodiments, the algorithm is further modified to reduce the percentage of discordant results in the training data set. In one embodiment, this is done by removing from the data set each data point that corresponds to a virus population comprising a mixture of mutations including the wild-type, at a single position considered by the algorithm tested. As shown in FIG. 3 and Example 3, this has the effect of reducing the number of PT-S, GT-R results, thus lowering the overall percentage of discordant results and so improves the fit of the algorithm to a training data set.

Figure 4:
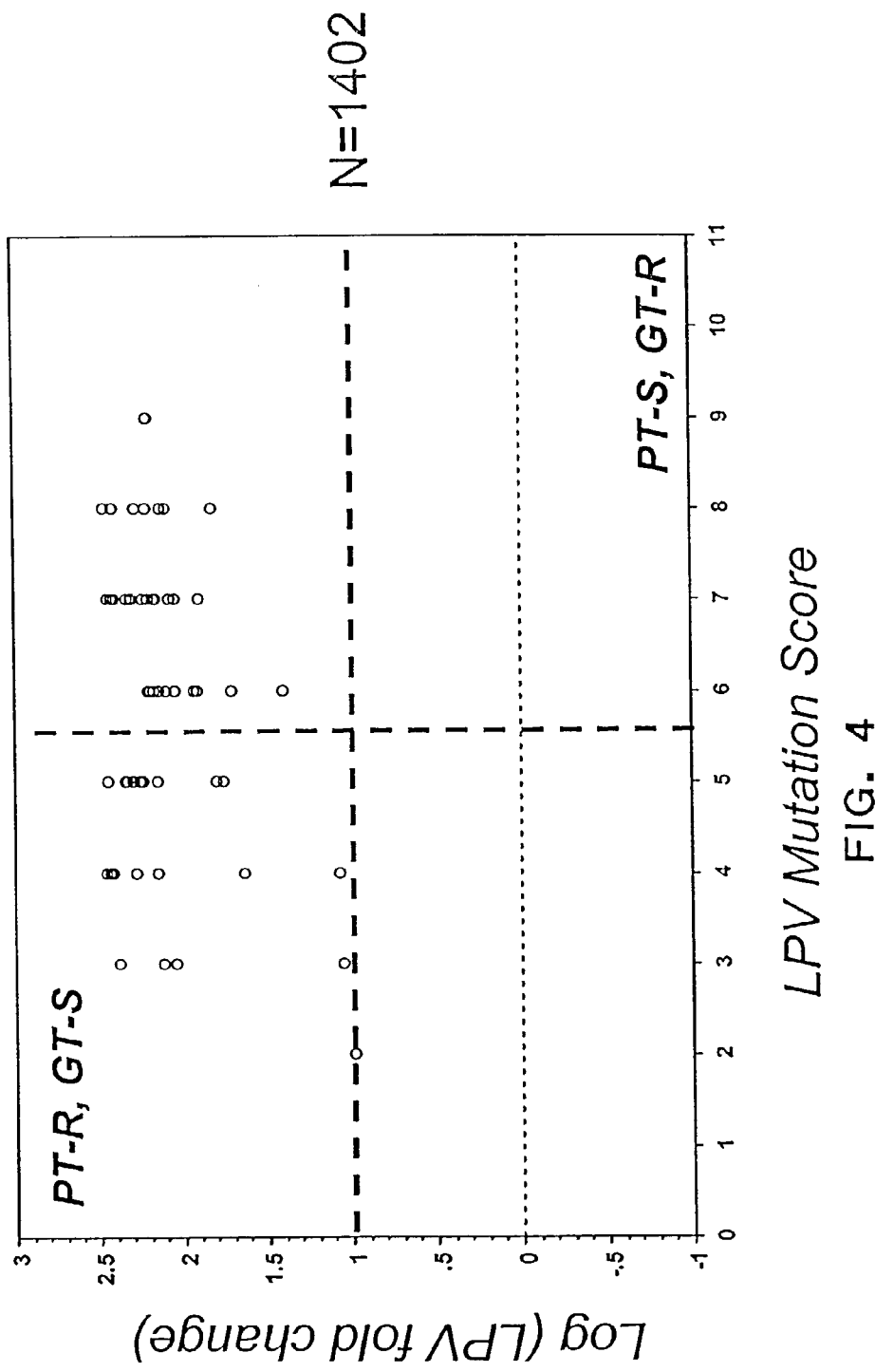
FIG. 4 is a scatter plot that shows the susceptibility to lopinavir (Log lopinavir fold change) of HIV samples containing the mutation I50V in the protease as a function of the total number of the resistance-associated mutations in those samples.

In another embodiment, the percentage of discordant results is reduced by assigning differential weight values to one or more mutations observed in the training data set. An algorithm that does not include this step assumes that each mutation in the training data set contributes equally to the overall resistance of a virus or population of viruses to an anti-viral therapy. In many cases this will not be true. FIG. 4 shows an example of a mutation in a training data set that is almost always correlated with phenotypic resistance to an anti-viral treatment. That is, almost every virus that has the mutation is phenotypically resistant to the anti-viral treatment, even those strains having only one or two total mutations. In one embodiment, such mutations are "weighted," i.e., assigned an increased mutation score. A mutation can be assigned a weight of, for example, two, three, four, five, six, seven, eight or more. For example, a mutation assigned a weight of 2 will be counted as two mutations in a virus. Fractional weighting values can also be assigned. In another embodiment, values of less than 1, and of less than zero, can be assigned, wherein a mutation is associated with an increased sensitivity of the virus to the anti-viral treatment.

One of skill in the art will appreciate that there is a tradeoff involved in assigning an increased weight to certain mutations. As the weight of the mutation is increased, the number of GT-R, PT-S discordant results may increase. Thus, assigning a weight to a mutation that is too great may increase the overall discordance of the algorithm. Accordingly, in one embodiment, a weight is assigned to a mutation that balances the reduction in GT-S, PT-R results with the increase in GT-R, PT-S results.

In another embodiment, the interaction of different mutations in the training data set with each other is also factored into the algorithm. For example, it might be found that two or more mutations behave synergistically, i.e., that the coincidence of the mutations in a virus contributes more significantly to the resistance of the virus than would be predicted based on the effect of each mutation independent of the other. Alternatively, it might be found that the coincidence of two or more mutations in a virus contributes less significantly to the resistance of the virus than would be expected from the contributions made to resistance by each mutation when it occurs independently. Also, two or more mutations may be found to occur more frequently together than as independent mutations. Thus, in one embodiment, mutations occurring together are weighted together. For example, only one of the mutations is assigned a weight of 1 or greater, and the other mutation or mutations are assigned a weight of zero, in order to avoid an increase in the number of GT-R, PT-S discordant results.

In another aspect, the phenotypic cutoff point can be used to define a genotypic cutoff point by correlating the number as well as the class of mutations in a virus of the data set with the phenotypic susceptibility of the virus. Examples of classes of mutations include, but are not limited to, primary amino acid mutations, secondary amino acid mutations, mutations in which the net charge on the polypeptide is conserved and mutations that do not alter the polarity, hydrophobicity or hydrophilicity of the amino acid at a particular position. Other classes of mutations that are within the scope of the invention, would be evident to one of skill in the art, based on the teachings herein.

In one embodiment, an algorithm is constructed that factors in the requirement for one or more classes of mutations. In another embodiment, the algorithm factors in the requirement for a minimum number of one or more classes of mutations. In another embodiment, the algorithm factors in the requirement for a minimum number of primary or secondary mutations. In another embodiment, the requirement for a primary or a secondary mutation in combination with other mutations is also factored into the algorithm. For example, it might be found that a virus with a particular combination of mutations is resistant to an anti-viral treatment, whereas a virus with any mutation in that combination, alone or with other mutations that are not part of the combination, is not resistant to the anti-viral treatment.

By using, for example, the methods discussed above, the algorithm can be designed to achieve any desired result. In one embodiment, the algorithm is designed to maximize the overall concordance (the sum of the percentages of the PT-R, GT-R and the PT-S, GT-S groups, or 100—(percentage of the PT-S, GT-R+PT-R, GT-S groups). In some embodiments, the overall concordance is greater than 75%, 80%, 85%, 90% or 95%. In one embodiment, the algorithm is designed to minimize the percentage of PT-R, GT-S results. In another embodiment, the algorithm is designed to minimize the percentage of PT-S, GT-R results. In another embodiment, the algorithm is designed to maximize the percentage of PT-S, GT-S results. In another embodiment, the algorithm is designed to maximize the percentage of PT-R, GT-R results.

At any point during the construction of the algorithm, or after it is constructed, it can be further tested on a second data set. In one embodiment, the second data set consists of viruses that are not included in the training data set, i.e., the second data set is a naive data set. In another embodiment, the second data set contains one or more viruses that were in the training data set and one or more viruses that were not in the training data set. Use of the algorithm on a second data set, particularly a naive data set, allows the predictive capability of the algorithm to be assessed. Thus, in one embodiment, the accuracy of an algorithm is assessed using a second data set, and the rules of the algorithm are modified as described above to improve its accuracy. In another embodiment, an iterative approach is used to create the algorithm, whereby an algorithm is tested and then modified repeatedly until a desired level of accuracy is achieved.

5.9 Using an Algorithm to Predict the Susceptibility of a Virus

In another aspect, the present invention also provides a method for using an algorithm of the invention to predict the phenotypic susceptibility of a virus or a derivative of a virus to an anti-viral treatment based on the genotype of the virus. In one embodiment, the method comprises detecting, in the virus or derivative of the virus, the presence or absence of one or more RAMs, applying the rules of the algorithm to the detected RAMs, wherein a virus that satisfies the rules of the algorithm is genotypically resistant to the anti-viral treatment, and a virus that does not satisfy the rules of the algorithm is genotypically sensitive to the anti-viral treatment. In another embodiment, the method comprises detecting, in the virus or derivative of the virus, the presence or absence of one or more RAMs, applying the rules of the algorithm to the detected RAMs, wherein a score equal to, or greater than the genotypic cutoff score indicates that the virus is genotypically resistant to the anti-viral treatment, and a score less than the genotypic cutoff score indicates that the virus is genotypically sensitive to the anti-viral treatment.

The algorithm of this invention can be used for any viral disease where anti-viral drug susceptibility is a concern, as discussed above in Section 5.4.1. In certain embodiments the assay of the invention can be used to determine the susceptibility of a retrovirus to an anti-viral drug. In one embodiment, the retrovirus is HIV. Preferably, the virus is HIV-1.

The anti-viral agent of the invention could be any treatment effective against a virus. It is useful to the practice of this invention, for example, to understand the structure, life cycle and genetic elements of the viruses which can be tested in the drug susceptibility test of this invention. These would be known to one of ordinary skill in the art and provide, for example, key enzymes and other molecules at which the anti-viral agent can be targeted. Examples of anti-viral agents of the invention include, but are not limited to, nucleoside reverse transcriptase inhibitors such as AZT, ddI, ddC, d4T, 3TC, abacavir, nucleotide reverse transcriptase inhibitors such as tenofovir, non-nucleoside reverse transcriptase inhibitors such as nevirapine, efavirenz, delavirdine, fusion inhibitors such as T-20 and T-1249 and protease inhibitors such as saquinavir, ritonavir, indinavir, nelfinavir, amprenavir and lopinavir.

In some embodiments of the invention, the anti-viral agents are directed at retroviruses. In certain embodiments, the anti-viral agents are protease inhibitors such as saquinavir, ritonavir, indinavir, nelfinavir, amprenavir and lopinavir. In one embodiment, the anti-viral agent is lopinavir.

Some mutations associated with reduced susceptibility to treatment with an anti-viral agent are known in the art. See, e.g., Kempf et al., 2001, *J. Virol.* 75:7462-69. Others can be determined by methods described in Sections 5.3-5.8 above. For example, Table 1 provides a list of mutations associated with reduced susceptibility to lopinavir.

5.10 Using an Algorithm to Predict the Effectiveness of Anti-Viral Treatment for an Individual In another aspect, the present invention also provides a method for using an algorithm of the invention to predict the effectiveness of an anti-viral treatment for an individual infected with a virus based on the genotype of the virus to the anti-viral treatment. In one embodiment, the method comprises detecting, in the virus or a derivative of the virus, the presence or absence of one or more RAMs, applying the rules of the algorithm to the detected RAMs, wherein a virus that satisfies the rules of the algorithm is genotypically resistant to the anti-viral treatment, and a virus that does not satisfy the rules of the algorithm is genotypically sensitive to the anti-viral treatment. In another embodiment, the method comprises detecting, in the virus or a derivative of the virus, the presence or absence of one or more RAMs, applying the rules of the algorithm to the detected RAMs, wherein a score equal to, or greater than the genotypic cutoff score indicates that the virus is genotypically resistant to the anti-viral treatment, and a score less than the genotypic cutoff score indicates that the virus is genotypically sensitive to the anti-viral treatment.

As described in Section 5.4.1 above, the algorithm of the invention can be used for any viral disease where anti-viral drug susceptibility is a concern and the anti-viral agent of the invention could be any treatment effective against a virus. In certain embodiments the assay of the invention is used to determine the susceptibility of a retrovirus to an anti-viral drug. In one embodiment, the retrovirus is HIV. Preferably, the virus is HIV-1. In some embodiments of the invention, the anti-viral agents are directed at retroviruses. In certain embodiments, the anti-viral agents are protease inhibitors such as saquinavir, ritonavir, indinavir, nelfinavir, amprenavir and lopinavir. In one embodiment, the anti-viral agent is lopinavir.

As described in Section 5.9 above, mutations associated with reduced susceptibility to treatment with an anti-viral agent may be obtained from the art or determined by methods described above in Sections 5.4-5.8.

In some embodiments, the present invention provides a method for monitoring the effectiveness of an anti-viral treatment in an individual infected with a virus and undergoing or having undergone prior treatment with the same or different anti-viral treatment, comprising, detecting, in a sample of said individual, the presence or absence of an amino acid residue associated with reduced susceptibility to treatment the anti-viral treatment wherein the presence of the residue correlates with a reduced susceptibility to treatment with the anti-viral treatment.

5.11 Correlating Susceptibility to one Anti-Viral Treatment with Susceptibility to Another Anti-Viral Treatment In another aspect, the present invention provides a method for using an algorithm of the invention to predict the effectiveness of an anti-viral treatment against a virus based on the genotypic susceptibility of the virus to a different anti-viral treatment. In one embodiment, the method comprises detecting, in a virus or a derivative of a virus, the presence or absence of one or more mutations correlated with resistance to an anti-viral treatment and applying the rules of an algorithm of the invention to the detected mutations, wherein a virus that satisfies the rules of the algorithm is genotypically resistant to the anti-viral treatment, and a virus that does not satisfy the rules of the algorithm is genotypically sensitive to the anti-viral treatment. In another embodiment, the method comprises detecting, in the virus or a derivative of the virus, the presence or absence of one or more mutations correlated with resistance to an anti-viral treatment and applying the rules of the algorithm to the detected mutations, wherein a score equal to, or greater than the genotypic cutoff score indicates that the virus is genotypically resistant to a different anti-viral treatment, and a score less than the genotypic cutoff score indicates that the virus is genotypically sensitive to a different anti-viral treatment. In another embodiment, the two anti-viral treatments affect the same viral protein. In another embodiment, the two anti-viral treatments are both protease inhibitors. Examples of protease inhibitors include, but are not limited to, saquinavir, ritonavir, indinavir, nelfinavir, amprenavir and lopinavir. In yet another embodiment, one of the two anti-viral treatments is lopinavir. In still another embodiment, a mutation correlated with resistance to one protease inhibitor is also correlated with resistance to another protease inhibitor. Examples of such mutations are provided in Example 8 below.

6. EXAMPLES

The following examples are provided to illustrate certain aspects of the present invention and not intended as limiting the subject matter thereof.

6.1 Example 1

Analysis of Patient Samples to Identify Resistance-Associated Mutations

This example demonstrates a method of analyzing patient samples so as to identify mutations that are associated either with increased or with decreased susceptibility to protease inhibitors such as lopinavir.

In order to determine the relationship between an HIV-1 strain's protease sequence and its susceptibility to treatment with lopinavir, a training data set of 2038 patient plasma samples was analyzed genotypically as well as phenotypically. The phenotypic assay was conducted using the PHENOSENSE™ (Virologic, South San Francisco, Calif.) HIV assay (Petropoulos et al., 2000, *Antimicrob. Agents Chemother.* 44:920-928; U.S. Pat. Nos. 5,837,464 and 6,242, 187). Plasma samples were collected from HIV-1-infected patients. Repeat samples from the same patient were removed to prevent possible bias resulting from unique combinations of mutations. $IC_{50}$ values for lopinavir were obtained for the HIV-1 from the patient sample. This was compared to the $IC_{50}$ for lopinavir against the NL4-3 (GenBank Accession No. AF324493) reference viral strain. Phenotypic data were expressed as "fold change" (or log fold change) in 50% inhibitory concentration ($IC_{50}$) of lopinavir. The fold $IC_{50}$ values were calculated by dividing the $IC_{50}$ of lopinavir against the HIV-1 from the patient plasma sample by the $IC_{50}$ for lopinavir against the NL4-3 (GenBank Accession No. AF324493) reference viral strain.

In order to define the genotypic changes correlated with reduced susceptibility to lopinavir, the entire amino acid sequences of HIV-1 proteases in each of the patients' samples were analyzed. Mutations were compared to the protease sequence of the NL4-3 (GenBank Accession No. AF324493) reference strain. Eighty eight out of ninety nine amino acid positions had at least one sample with a mutation (Tables 2 and 3). In the 2038 samples in the training data, there were 61 positions that were mutated in 1% or more of the samples (i.e., more than 20 samples), leaving 38 positions with mutations in 20 or fewer samples (less than 1% of the samples). This data is listed in Tables 2 and 3. Table 1 provides a list of mutations associated with reduced susceptibility to lopinavir. The data in Table 1 were obtained either with the entire training data set of 2038 samples or with a data set of 1418 samples (indicated with an *), after the removal of samples without any primary mutations associated with protease inhibitors and without an $IC_{50}$ fold change ("FC") greater than two for any protease inhibitor (Example 5). The method used to calculate P values is described in Example 5.

6.2 Example 2

Correlation of Lopinavir Susceptibility to Number of Mutations in HIV-1 Protease This example demonstrates that a simple algorithm that correlates the number of equally-weighted mutations in the protease gene of an HIV-1 with its susceptibility to lopinavir is inaccurate.

A data set of 2038 patient plasma samples was analyzed and mutations associated with reduced susceptibility to lopinavir were identified, as described in Example 1. The phenotypic susceptibility to lopinavir (lopinavir fold change) was analysed as a function of the number of mutations in the protease of the HIV-1 present in a patient's plasma sample. The fold change for each sample was calculated by dividing the $IC_{50}$ of lopinavir against the HIV-1 from the patient's plasma sample by the $IC_{50}$ for lopinavir against the NL4-3 (GenBank Accession No. AF324493) reference viral strain. The genotype data was obtained by sequencing the protease of the HIV-1 present in each patient's sample and determining the sequence changes with respect to the sequence of the NL4-3 (GenBank Accession No. AF324493) HIV. The amino sequence for the NL4-3 protease is provided in SEQ. ID. No. 1 (FIG. 12A) and the nucleic acid sequence for the NL4-3 protease gene is provided in SEQ. ID. No. 2 (FIG. 12B).

FIG. 2 shows the resistance to lopinavir (Log lopinavir fold change) as a function of the number of the resistance-associated mutations. Samples with mixtures of amino acids were treated as mutants. The mutations used in this analysis were those identified in the Kempf study (Kempf et al., 2001, *J. Virol.* 75:7462-69). In order to clearly demonstrate the shortcomings of an algorithm proposed by Kempf, which attempted to predict the phenotypic susceptibility to lopinavir based on the number of mutations observed at 11 identified positions in HIV protease, the graph for this analysis was divided into four quadrants. The Kempf study postulated that HIV was sensitive to treatment with lopinavir if it had five or fewer mutations at these 11 positions, but, if the number of these mutations was six or more, then the virus was predicted to be resistant to lopinavir treatment. The bottom left quadrant corresponds to those viruses which contain 5 or fewer mutations in their protease and which are phenotypically and genotypically sensitive (PT-S, GT-S) to lopinavir. 1109, or 54% of the 2038 samples were found in this quadrant. The top right quadrant corresponds to those viruses which contain six or more mutations and are phenotypically and genotypically resistant (PT-R, GT-R) to lopinavir (Log lopinavir fold change $\geqq 1$) and contained 637 or 31% of the samples. However, the other two quadrants correspond to the "exceptions" where a virus was predicted based on genotype (number of mutations) to be susceptible, but was phenotypically (based on Log lopinavir fold change) resistant (left top, PT-R, GT-S) or where a virus was predicted based on genotype to be resistant, but was phenotypically (based on Log lopinavir fold change) susceptible (right bottom, PT-S, GT-R).

FIG. 2 shows that 182 samples, corresponding to 9% of the starting set, with two to five mutations, contrary to expectations, are found in the top, left (PT-R, GT-S) quadrant and exhibit $IC_{50}$ values as much as 10- to 100-fold higher than the $IC_{50}$ for the reference strain (log fold change is 1-2). Conversely, some viruses that had six, seven, or eight mutations did not exhibit any greater resistance to lopinavir than did the WT strain, and so appear in the bottom, right (PT-S, GT-R) quadrant (110 samples (5%)).

It is thus evident from FIG. 2 that a simple correlation of susceptibility to lopinavir with the number of mutations in the HIV-1 protease is far from accurate.

6.3 Example 3

Reducing the Size of the PT-S, GT-R Discordant Group

This example demonstrates that the PT-S, GT-R data seen in FIG. 2 can be accounted for by the presence of samples containing mixtures of amino acids in at least one lopinavir resistance-associated position.

Using the simple algorithm of Example 2 produced approximately 9% results in the top, left ("PT-R, GT-S") quadrant and 5% results in the bottom, right ("PT-S, GT-R") quadrant (FIG. 2). These discordant results could be attributed, at least in part, to patients' samples that contained a mixture of viral strains with proteases that had a mixture of amino acid residues at one or more positions associated with reduced susceptibility to lopinavir. When these samples (i.e. those samples that contained a mixture of both, a wild-type and a mutant) were excluded from the analysis, the PT-S, GT-R results decreased to 2% whereas the number of PT-R, GT-S results stayed about the same at 10% (FIG. 3). 1402 samples were used in this modified analysis.

Without being bound by any particular theory, this can be explained by the following hypothesis. The study treated samples which contained mixtures of viral strains as mutants. This could, therefore, have resulted in treating a sample which contained 10% mutant virus (containing a resistance-associated mutation) and 90% unmutated or reference virus as a mutant. Because of the small population of mutant virus, the overall sample may not exhibit as much phenotypic resistance as would be expected if the sample contained 100% mutant. However, for genotypic purposes, the sample is treated as containing a mutation. Such samples could therefore lead to the observation of lower phenotypic resistance than expected for a sample with 100% mutant. This results in data that fall into the bottom, right quadrant where the population is genotypically resistant (GT-R), but phenotypically sensitive (PT-S).

Removal of samples containing mixtures of amino acids at one or more positions associated with reduced susceptibility to lopinavir clearly reduced the PT-S, GT-R results, thereby demonstrating the link between the two.

6.4 Example 4

Analysis of the PT-R, GT-S Discordant Group

This example demonstrates that certain mutations make a greater contribution to lopinavir resistance than others.

The samples in the PT-R, GT-S quadrant of FIG. 2 correspond to viruses with five or fewer mutations in the HIV protease associated with reduced susceptibility to lopinavir. These viruses were phenotypically resistant (had a fold change greater than 10) but were predicted to be genotypically sensitive (because they had five or fewer mutations). Without being bound by any particular theory, this can be explained by some mutations contributing more significantly to lopinavir resistance than other mutations. Some of these mutations may even confer as much resistance to lopinavir as four or five of the other lopinavir-associated mutations. When these, more significant mutations are present along with one, two, three or four other lopinavir-associated mutations, the total resistance conferred may be large enough to make the virus phenotypically resistant.

Figure 5:
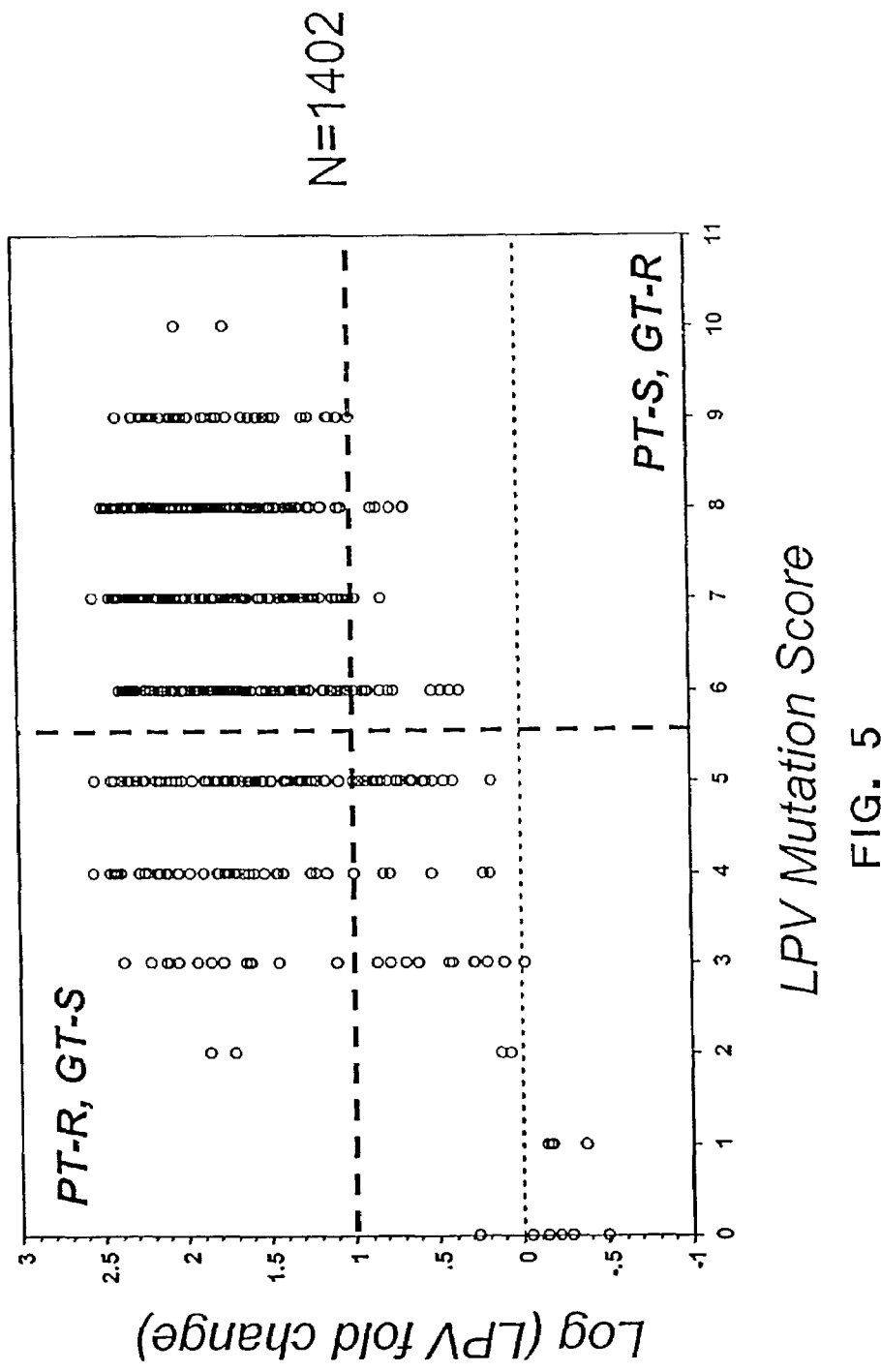
FIG. 5 is a scatter plot that shows the susceptibility to lopinavir (Log lopinavir fold change) of HIV samples containing the mutations V82A, F, S, T or I in the protease as a function of the total number of the resistance-associated mutations in those samples.

Mutations that were significantly associated with the PT-R, GT-S group were seen at positions 50, 54 and 82. Table 1 provides a list of mutations associated with reduced susceptibility to lopinavir. FIGS. 4, 5 and 6 demonstrate that when the more significant mutations (those at positions 50, 54 and 82) are present, the lopinavir fold change is high and the samples are mostly in the top half of the graph—that half associated with increased phenotypic resistance. A comparison of FIGS. 2 or 3 with FIGS. 4, 5 and 6 also demonstrates that most of the samples in the PT-R, GT-S quadrant are those that contain the more significant mutations.

Thus, it is evident that the PT-R, GT-S group can be associated with the presence of mutations that confer disproportionately more resistance to lopinavir than others.

6.5 Example 5

Alternate Analysis of Patient Samples to Identify Resistance-Associated Mutations This example demonstrates (1) an alternate method of analyzing patient samples so as to identify mutations that are associated either with increased or with decreased susceptibility to protease inhibitors such as lopinavir; (2) that a simple algorithm that correlates the number of equally-weighted mutations in the protease gene of an HIV with its susceptibility to lopinavir is inaccurate (3) that the data seen in the PT-S, GT-R quadrant can be accounted for by the presence of samples containing mixtures of amino acids in at least one lopinavir resistance-associated position; and (4) that certain mutations make a greater contribution to lopinavir resistance than others.

In order to determine the relationship between an HIV-1 strain's protease sequence and its susceptibility to treatment with lopinavir, a training data set of 2038 patient plasma samples was analyzed genotypically as well as phenotypically. From the starting point of 2038 samples, those samples that did not have any evidence of reduced protease inhibitor susceptibility by both phenotype and genotype were then removed. The phenotypic criterion for this exclusion was all samples having LPV FC<2 and the genotypic criterion was no mutations at any of the following (primary) positions: 30, 32, 46, 48, 50, 54, 82 (except V82I), 84, 88, or 90. This resulted in the elimination of 620 samples, leaving a data set of 1418 samples that were analyzed as in Example 1.

Similar to FIG. 2, resistance to lopinavir (Log lopinavir fold change) was plotted as a function of the number of the resistance-associated mutations. FIG. 7 shows a plot of the data obtained in this analysis (of 1418 samples). FIG. 7, just like FIG. 2, also contains data in all four quadrants. Of the 1418 samples analyzed, 45% (637 samples) were PT-R, GT-R, 34% (489 samples) were PT-S, GT-S, 13% (182 samples) were PT-R, GT-S and 8% (110 samples) were PT-S, GT-R.

When, as in Example 3, the samples containing a mixture of viral strains with proteases that had a mixture of amino acid residues at one or more positions associated with reduced susceptibility to lopinavir were excluded from the analysis, the number of samples in the PT-S, GT-R quadrant decreased to 4% (31 samples). This analysis resulted in the exclusion of 555 samples, leaving a total of 863 samples (FIG. 8).

As in Example 4, mutations that were significantly associated with the PT-R, GT-S group were seen at positions 50, 54 and 82. FIGS. 9, 10 and 11 demonstrate that when the more significant mutations (those at positions 50, 54 and 82) are present, the lopinavir fold change is high and the samples are mostly in the top half of the graph—that half associated with increased phenotypic resistance. A comparison of FIGS. 7 or 8 with FIGS. 9, 10 and 11 also demonstrates that most of the samples in the PT-R, GT-S quadrant are those that contain the more significant mutations.

P values for determining the statistical significance of the correlations were calculated as follows: for each mutation the number of samples in the data set (here, genotypically sensitive samples from the N=863 data set) that were below or above 10-fold for LPV were compared in samples with or without the mutation in question. A 2×2 table was constructed and the P value was calculated using Fisher's Exact test. An example is shown for G48V:

| G48V | PT-S | PT-R | p-value |
|---|---|---|---|
| absent | 275 | 97 | 2.87E−19 |
| present | 7 | 50 | |

6.6 Example 6

First Refined Algorithm and Demonstration of its Improved Accuracy

This example demonstrates that an algorithm can be constructed that reduces the incidence of PT-R, GT-S results by differentially weighting the contribution of mutations that contribute more significantly to lopinavir resistance.

As described in Example 5, from a starting training data set of 2038 samples, those samples without any primary mutations associated with protease inhibitors and those samples without an $IC_{50}$ fold change ("FC") greater than two for any protease inhibitor were eliminated, resulting in a data set of 1418 samples. Further exclusion of samples containing a mixture of viral strains with proteases that had a mixture of amino acid residues at one or more positions associated with reduced susceptibility to lopinavir, resulted in a final data set of 863 samples which were used to design an algorithm that can accurately predict the susceptibility of HIV to lopinavir by reducing the incidence of PT-R, GT-S results.

The final rules were formulated based on the results observed only in the training data set (863 samples). The rules devised from the training data set were then tested on the training data set and a second set of samples ("validation set"). The validation data set contained 1022 samples and excluded any samples from patients included in the training data set. As for the training data, samples with no evidence of reduced susceptibility to protease inhibitors were removed, leaving 523 samples. The accuracy of the devised rules or algorithm was decided on the accuracy with which the susceptibility of the patients could be determined based solely on the algorithm. When discrepancies were seen, the algorithm was modified so that it remained consistent with the results seen in the training set.

The modified algorithm was then tested again on the validation set. The results seen in the second version were better than those of the initial version. This process was repeated many times and each version of the results was at least as good, if not better, than the version before it.

Tables 4, 5 and 6 provide a summary of the rules applied at each round or version and the results obtained in the training data set (Table 4) and two different validation sets (Tables 5 and 6). The first column provides the round or version number. The next four columns provide, in order, the numbers expected, according to the algorithm, in the PT-S, GT-R, the PT-R, GT-R, the PT-S, GT-S, PT-R, GT-S groups. The next two columns provide the percentage of the PT-S, GT-R and PT-R, GT-S groups. The next column provides the overall concordance (the sum of the percentages of the PT-R, GT-R and the, PT-S, GT-S groups, or 100—(percentage of the PT-S, GT-R+PT-R, GT-S groups).

The last column contains the rules used for that round of testing. Each set of rules is added to the rules preceding it. Some mutations were weighted higher than others (e.g., most of the V82 and I54 mutations), some were removed altogether from the analysis (e.g., I54L) and the weighting factors of some were altered in progressive versions of the algorithm. In version 6, the weighting factor for all V82 mutants was increased from 1 to 3. For version 7, however, the weighting factor for V82T was decreased back to 1, because it did not contribute to resistance to lopinavir as significantly as the other V82 mutants did. FIG. 13 shows the effect of the various amino acid (wild-type and mutations) at position 82. One can see that the effect of V82T on the lopinavir fold change is not as large as the other V82 mutants. A preliminary analysis of the I54 mutants resulted in the removal of I54L from the algorithm. However, a subsequent analysis showed that I54L makes a significant contribution to lopinavir resistance (FIG. 14). Thus, in Table 7, I54L has been assigned a weighting factor of 1, although it is not included in the algorithm as presented in Table 4. Without being bound by any particular theory, I54L was removed from the algorithm because it is a relatively rare mutation and therefore does not occur frequently in the data set. Because it is rare, it may have little or no effect on the analysis of a large collection of samples, but, when present in a particular virus, or virus from a particular patient, it contributes significantly to lopinavir resistance.

As one goes from "start" to version 10, the overall concordance for all 3 sets of data increases and that the percentage of data in the PT-R, GT-S group decreases dramatically; nearly 7-fold in the training data set and about 6-fold in the validation data sets.

Table 7 provides a list of weights or weighting factors assigned to each mutation. This table can be used to predict whether a particular HIV strain is likely to have reduced susceptibility to lopinavir. Each of the protease mutations listed in Table 7 that is detected in the strain is assigned a weighting factor according to Table 7. The weighting factors are then added to get a total score for the HIV. If the total score is 6 or more, then the HIV is likely to be resistant to treatment with lopinavir and if the total score is less than 6, then the HIV is likely to be sensitive to treatment lopinavir.

6.7 Example 7

Second Refined Algorithm and Demonstration of its Improved Accuracy

This example demonstrates that an algorithm can be constructed that reduces the incidence of PT-R, GT-S and PT-S, GT-R results by adjusting the total score required in order for a particular HIV strain to be considered genotypically resistant or susceptibile to treatment with lopinavir.

A combined data set of 2195 samples, i.e., a data set consisting of the "training data set" and the "validation data set," was analyzed. Samples were excluded that did not have a primary mutation associated with phenotypic resistance to protease inhibitors, were not correlated to an $IC_{50}$ fold change ("FC") greater than two for any protease inhibitor, or that contained a mixture of viral strains having proteases with different amino acid residues at a position associated with reduced susceptibility to lopinavir if the mixture included the amino acid found at that position in the NL4-3 HIV strain. A final data set of 1099 samples was used to alter the algorithm described in Example 6 so as to improve its overall concordance.

The same weighting factors listed in Table 7 were used. In the changed algorithm, the cutoff value was changed from 6 to 8, i.e., if the total score for a particular HIV was 8 or greater, then the HIV was genotypically resistant to treatment with lopinavir and if the total score was less than 8, then the HIV was genotypically sensitive to treatment with lopinavir. Using a cutoff value of 8, the overall concordance, 90.5%, was higher than that seen with a cutoff value of 6 (Table 8). FIG. 15 provides a scatter plot using a cutoff value of 8. The reduction in PT-R, GT-S and PT-S, GT-R results compared to FIGS. 2 and 7 can be seen. An even higher overall concordance of 91.5% was observed when a cutoff value of 7 was used in the algorithm (Table 8). This is seen in FIG. 16.

6.8 Example 8

Effect of Mutations Associated with Amprenavir Resistance on Lopinavir Resistance This example demonstrates that certain mutations correlated with an increase in Amprenavir ("APV") resistance of HIV are also correlated with an increased resistance to lopinavir.

FIG. 17 shows the effect of protease mutations associated in HIV with resistance to Amprenavir ("APV") on resistance to lopinavir. HIV-1 isolates with a decreased susceptibility to amprenavir have been selected in vitro and obtained from patients treated with amprenavir. Genotypic analysis of these isolates showed that resistance to APV is associated with 8 mutations in the HIV-1 protease gene: 5 primary (V32I, I50V, I54L/M, and I84V) and 3 secondary (M46I/L and I47V). See Maguire et al., 2002, *Antimicrob Agents Chemother* 46:731-738. Without exception, each of these mutations is correlated with reduced susceptibility to lopinavir (Table 1). V32I and I47V are also known to be selected by LPV in vitro. Carrillo et al., 1998, *J. Virol.* 72:7532-41. The effect of these mutations and combinations of these mutations with each other and I84V on LPV and APV susceptibility is summarized in Table 9. The median FC for APV was 9.5-fold or higher in each group, as might be expected. However the median LPV FC often paralleled, and was often greater than that of APV. This observation led to the investigation of the degree of cross-resistance between these two protease inhibitors.

From a list of 26 mutations associated with APV FC≧2.5 based on univariate analysis, 23 were also associated with LPV FC≧2.5 (Table 10). Using regression analysis, the correlation between FC (log-transformed) for the two PIs was analyzed. FIG. 18 shows a bivariate scatter plot of lopinavir fold change ("Log LPV FC") versus amprenavir fold change ("Log APV FC"). The darker dots ("APV GT-R" in the legend) represent those samples that were genotypically resistant to amprenavir and the ligther dots ("APV GT-S" in the legend) represent those samples that were genotypically sensitive to amprenavir. FIG. 18 shows that the correlation between amprenavir and lopinavir is higher for those samples that are genotypically resistant to amprenavir (correlation coefficient, $R^2$=0.52) than for those that are genotypically sensitive to amprenavir (correlation coefficient, $R^2$=0.39) (all samples with FC<2.5 for either protease inhibitor were excluded for this analysis). Seventy-six percent of all samples, and 82% of APV GT-R samples, that were PT-R to either protease inhibitor were resistant to both. While 95% of samples defined as GT-R for APV were also PT-R, 80% were also. PT-R for LPV (Table 11).

Despite the correlation, the presence of APV mutations alone was not sufficient for LPV FC>10, requiring accumulation of 8 or more mutations from those associated with reduced susceptibility to LPV (i.e., those listed in Table 1).

All references cited herein are incorporated by reference in their entireties.

The examples provided herein, both actual and prophetic, are merely embodiments of the present invention and are not intended to limit the invention in any way.

TABLE 1

| | Lopinavir Mutations | | | |
|---|---|---|---|---|
| Mutation | FC < 10 | FC ≧ 10 | % R:% S | P value |
| L10F | 16 | 25 | 9 | <0.0001 |
| L10F* | 15 | 25 | 3 | 0.0001 |
| L10I* | 105 | 97 | 2 | <0.0001 |
| G16E* | 8 | 23 | 6 | <0.0001 |
| K20I | 21 | 24 | 6 | <0.0001 |
| K20I* | 14 | 24 | 3 | 0.0001 |
| K20M | 6 | 10 | 9 | <0.0001 |
| K20M* | 4 | 10 | 5 | 0.0045 |
| K20R | 17 | 13 | 4 | 0.0002 |
| L24I | 7 | 10 | 8 | <0.0001 |
| V32I | 9 | 18 | 11 | <0.0001 |

TABLE 1-continued

| | Lopinavir Mutations | | | |
|---|---|---|---|---|
| Mutation | FC < 10 | FC ≧ 10 | % R:% S | P value |
| V32I* | 9 | 18 | 4 | 0.0004 |
| L33IFV** | 38 | 47 | 7 | <0.0001 |
| L33F* | 14 | 42 | 6 | <0.0001 |
| E34DKQ** | 4 | 18 | 25 | <0.0001 |
| E34Q* | 2 | 12 | 12 | 0.0001 |
| K43T* | 4 | 22 | 11 | <0.0001 |
| M46I | 49 | 57 | 6 | <0.0001 |
| M46L | 16 | 19 | 7 | <0.0001 |
| M46I* | 49 | 57 | 2 | <0.0001 |
| M46L* | 16 | 19 | 2 | 0.009 |
| M46V* | Not Available | Not Available | Not Available | Not Available |
| I47V* | 5 | 22 | 8 | <0.0001 |
| I47A | Not Available | Not Available | Not Available | Not Available |
| I47V | 5 | 22 | 25 | <0.001 |
| G48V | 7 | 50 | 40 | <0.0001 |
| G48V* | 7 | 50 | 14 | <0.0001 |
| I50V | 1 | 22 | 123 | <0.0001 |
| I50V* | 1 | 25 | 48 | <0.0001 |
| I54A | 0 | 22 | -N/A- | <0.0001 |
| I54L | Not Available | Not Available | Not Available | Not Available |
| I54M | 6 | 21 | 20 | <0.0001 |
| I54S | 0 | 14 | -N/A- | <0.0001 |
| I54T | 0 | 5 | -N/A- | <0.0001 |
| I54V | 7 | 47 | 37 | <0.0001 |
| I54A* | 0 | 22 | -N/A- | <0.0001 |
| I54M* | 6 | 21 | 7 | <0.0001 |
| I54S* | 0 | 14 | -N/A- | <0.0001 |
| I54T* | 0 | 5 | -N/A- | 0.0045 |
| I54V* | 7 | 47 | 13 | <0.0001 |
| K55R | 13 | 12 | 5 | <0.0001 |
| Q58E | 19 | 26 | 8 | <0.0001 |
| Q58E* | 18 | 26 | 3 | 0.0003 |
| L63T* | 4 | 11 | 5 | 0.002 |
| I66FV** | 14 | 12 | 5 | 0.0001 |
| A71I | 5 | 7 | 8 | 0.0007 |
| G73C | 2 | 6 | 17 | 0.0002 |
| G73T | 10 | 13 | 7 | <0.0001 |
| T74ASP** | 27 | 37 | 8 | <0.0001 |
| T74S* | 14 | 25 | 3 | 0.0001 |
| L76V | 1 | 6 | 34 | <0.0001 |
| L76V* | 1 | 6 | 12 | 0.0076 |
| P79ADE** | 3 | 6 | 11 | 0.0006 |
| V82A | 14 | 73 | 29 | <0.0001 |
| V82F | 2 | 6 | 17 | 0.0002 |
| V82A* | 14 | 73 | 10 | <0.0001 |
| V82S | 0 | 7 | -N/A- | <0.0001 |
| V82S* | 0 | 7 | -N/A- | 0.0005 |
| I84A* | Not Available | Not Available | Not Available | Not Available |
| I84L* | Not Available | Not Available | Not Available | Not Available |
| I84V | 41 | 33 | 4 | <0.0001 |
| L89I* | 0 | 5 | -N/A- | 0.0045 |
| L89M* | 7 | 13 | 4 | 0.0004 |

Number of starting samples = 2038.
*Number of starting samples = 1418 (after the removal of samples without any primary mutations associated with protease inhibitors and without an $IC_{50}$ fold change ("FC") greater than two for any protease inhibitor).
**All variants treated equally.
-N/A-: Not Applicable (results in a division by zero).
FC: Fold Change in $IC_{50}$.
% R: Percent of samples with mutation compared to all PT-R, GT-S samples.
% S: Percent of samples with mutation compared to all PT-S, GT-S samples.

TABLE 2

Correlation of Number of Positions With Number of Samples With a Mutation

| Number of Positions | Number of Samples With Mutations |
|---|---|
| 11 | 0 |
| 9 | 1 |
| 3 | 2 |
| 2 | 3 |
| 2 | 4 |
| 3 | 5 |
| 1 | 6 |
| 3 | 7 |
| 0 | 8 |
| 0 | 9 |
| 34 | <10 |
| 65 | >10 |
| 61 | >20 |
| 46 | >100 |
| 4 | 10 to 20 |
| 15 | 20 to 100 |

TABLE 3

Number of Samples Seen With Mutations at Each Position of HIV Protease

| Position | Number of Samples |
|---|---|
| P1 | 0 |
| P9 | 0 |
| D25 | 0 |
| G27 | 0 |
| D29 | 0 |
| T31 | 0 |
| P44 | 0 |
| G78 | 0 |
| G86 | 0 |
| L97 | 0 |
| N98 | 0 |
| Q2 | 1 |
| T26 | 1 |
| A28 | 1 |
| G49 | 1 |
| G52 | 1 |
| V56 | 1 |
| P81 | 1 |
| G94 | 1 |
| F99 | 1 |
| I3 | 2 |
| L5 | 2 |
| G40 | 2 |
| W6 | 3 |
| W42 | 3 |
| R87 | 4 |
| T96 | 4 |
| R8 | 5 |
| G51 | 5 |
| Y59 | 5 |
| T80 | 6 |
| Q7 | 7 |
| E21 | 7 |
| G68 | 7 |
| V75 | 12 |
| G17 | 13 |
| L38 | 17 |
| L23 | 20 |
| T4 | 24 |
| A22 | 24 |
| N83 | 25 |
| E65 | 33 |
| P79 | 39 |
| T91 | 39 |
| K45 | 45 |
| L76 | 57 |
| C95 | 59 |
| P39 | 61 |
| Q18 | 63 |
| D30 | 74 |
| I50 | 80 |
| N88 | 89 |
| K70 | 96 |
| E34 | 101 |
| I66 | 103 |
| C67 | 110 |
| I47 | 112 |
| V32 | 116 |
| V11 | 117 |
| Q92 | 121 |
| I85 | 131 |
| L24 | 134 |
| G16 | 136 |
| Q61 | 144 |
| K55 | 153 |
| G48 | 156 |
| F53 | 159 |
| Q58 | 159 |
| L89 | 186 |
| T74 | 202 |
| K43 | 208 |
| K14 | 210 |
| H69 | 213 |
| R57 | 237 |
| T12 | 244 |
| D60 | 247 |
| L19 | 297 |
| L33 | 411 |
| G73 | 416 |
| I64 | 458 |
| I84 | 482 |
| I15 | 489 |
| I72 | 518 |
| R41 | 534 |
| I13 | 556 |
| K20 | 631 |
| V77 | 708 |
| E35 | 735 |
| V82 | 741 |
| M46 | 780 |
| I93 | 823 |
| N37 | 826 |
| I54 | 834 |
| M36 | 841 |
| I62 | 897 |
| L90 | 946 |
| A71 | 1047 |
| L10 | 1242 |
| L63 | 1858 |

TABLE 4

Algorithm Construction and Application to the Training Data

| No. | PT-S, GT-R | PT-R, GT-R | PT-S, GT-S | PT-R, GT-S | % PT-R, GT-S | % PT-S, GT-R | Concordance | Rules |
|---|---|---|---|---|---|---|---|---|
| Start | 32 | 412 | 281 | 138 | 16.0% | 3.7% | 80.3% | All mutations weighted equally |
| 1 | 36 | 457 | 277 | 93 | 10.8% | 4.2% | 85.1% | Added M46V, I50V (weight = 3), I54AMS, I84AL, V82S |
| 6 | 58 | 519 | 255 | 31 | 3.6% | 6.7% | 89.7% | Added L33F, I47V, G48MV, L63T, increased V82AFST weight to 3 |
| 7 | 56 | 517 | 257 | 33 | 3.8% | 6.5% | 89.7% | V82T weight set back to 1 |
| 8 | 57 | 522 | 256 | 28 | 3.2% | 6.6% | 90.2% | Add V32I, E34Q, K43T, L89IM, remove I54L |
| 10 | 65 | 530 | 248 | 20 | 2.3% | 7.5% | 90.2% | Add 58E, 74S, 76V, increase weight of 54 to 3x |

TABLE 5

Application of Algorithm to Validation Data Set 1

| No. | PT-S, GT-R | PT-R, GT-R | PT-S, GT-S | PT-R, GT-S | % PT-R, GT-S | % PT-S, GT-R | Overall Concordance |
|---|---|---|---|---|---|---|---|
| Start | 37 | 130 | 302 | 54 | 10.3% | 7.1% | 82.6% |
| 1 | 38 | 140 | 301 | 44 | 8.4% | 7.3% | 84.3% |
| 10 | 66 | 175 | 273 | 9 | 1.7% | 12.6% | 85.7% |

Number of samples in data set=523.

TABLE 6

Application of Algorithm to Validation Data Set 2

| No. | PT-S, GT-R | PT-R, GT-R | PT-S, GT-S | PT-R, GT-S | % PT-R, GT-S | % PT-S, GT-R | Overall Concordance |
|---|---|---|---|---|---|---|---|
| Start | 8 | 86 | 172 | 41 | 13.4% | 2.6% | 84.0% |
| 1 | 8 | 94 | 172 | 33 | 10.7% | 2.6% | 86.6% |
| 10 | 25 | 120 | 155 | 7 | 2.3% | 8.1% | 89.6% |

Number of samples in data set=307 (after the removal of samples containing mixtures of amino acids at any of the positions associated with reduced susceptibility to lopinavir from the starting data set of 523 samples of Table 7).

TABLE 7

Weighting Factors

| Mutation | Weighting Factor |
|---|---|
| L10F | 1 |
| L10I | 1 |
| G16E | 1 |
| K20I | 1 |
| K20M | 1 |
| K20R | 1 |
| L24I | 1 |
| V32I | 1 |
| L33F | 1 |
| E34Q | 1 |
| K43T | 1 |
| M46I | 1 |
| M46L | 1 |

TABLE 7-continued

Weighting Factors

| Mutation | Weighting Factor |
|---|---|
| M46V | 1 |
| I47V | 1 |
| G48V | 1 |
| I50V | 3 |
| I54A | 3 |
| I54L | 1 |
| I54M | 3 |
| I54S | 3 |
| I54T | 3 |
| I54V | 3 |
| K55R | 1 |
| Q58E | 1 |
| L63T | 1 |
| A71I | 1 |
| L76V | 1 |
| V82A | 3 |
| V82F | 3 |
| V82S | 3 |
| V82T | 1 |
| I84A | 1 |
| I84L | 1 |
| I84V | 1 |
| L89I | 1 |
| L89M | 1 |

TABLE 8

Analysis of Combined Data Set

| Cutoff Value | PT-S, GT-S | PT-S, GT-S | PT-R, GT-R | PT-R, GT-S | Overall Concordance |
|---|---|---|---|---|---|
| 6 | 93 | 404 | 589 | 13 | 90.4% |
| 7 | 63 | 434 | 572 | 30 | 91.5% |
| 8 | 50 | 447 | 548 | 54 | 90.5% |

TABLE 9

EFFECT OF APV MUTATIONS ON LPV AND APV SUSCEPTIBILITY

| genotype group | n | Median LPV FC | Median APV FC |
|---|---|---|---|
| wild-type (all primary positions) | 623 | 0.6 | 0.6 |
| not containing any tested mutation | 1096 | 2.1 | 1.6 |
| 32 | 26 | 12 | 9.5 |
| 47 | 8 | 191 | 26 |
| 50 | 42 | 54 | 20 |
| 54[a] | 9 | 160 | 22 |
| 84 | 247 | 7.1 | 11 |
| 32, 47 | 23 | 7.5 | 12 |
| 32, 84 | 3 | 124 | 51 |
| 46[b], 54 | 16 | 138 | 84 |
| 47, 54 | 3 | 88 | 42 |
| 47, 84 | 4 | 28 | 12 |
| 54, 84 | 22 | 93 | 67 |
| 32, 47, 54 | 17 | 146 | 40 |
| 46, 54, 84 | 29 | 30 | 47 |
| 47, 54, 84 | 3 | 20 | 24 |
| 32, 46, 47, 54 | 4 | 208 | 130 |
| 32, 47, 54, 84 | 5 | 227 | 130 |
| 32, 46, 47, 54, 84 | 6 | 200 | 130 |

[a]I54L or M only
[b]M46I or L

TABLE 10

MUTATIONS ASSOCIATED WITH APV AND LPV FC > 2.5

| APV | APV/LPV |
|---|---|
| 10F | 10F |
| 11 | 11 |
| 23 | |
| 32I | 32I |
| 33F | 33F |
| 34Q | 34Q |
| 43T | 43T |
| 47V | 47V |
| 48M | 48M |
| 50V | 50V |
| 53L | 53L |
| 54A | 54A |
| 54L | 54L |
| 54M | 54M |
| 54S | 54S |
| 54T | 54T |
| 55 | 55 |
| 58E | 58E |
| 66 | |
| 71L | 71L |
| 76V | 76V |
| 79 | 79 |
| 82F | 82F |
| 84V | 84V |
| 92 | |
| 95 | 95 | mutations with % R:% S > 5 and P < 0.01, for FC > 2.5

TABLE 11

SUMMARY STATISTICS FOR LPV-APV CROSS-RESISTANCE

| | Percent of Samples | |
|---|---|---|
| category | All[a] | APV GT-R |
| APV FC > 2.5 also LPV FC > 10 | 82 | 83 |
| LPV FC > 10 also APV FC > 2.5 | 91 | 99 |
| PT-R for either PI PT-R for both | 76 | 82 |
| APV FC > 2.5 | 61 | 95 |
| LPV FC > 10 | 55 | 80 |

[a]samples with no protease inhibitor FC > 2 and no protease inhibitor primary mutations excluded; n = 1099

What is claimed is:

1. A method for determining whether a human immunodeficiency virus (HIV) has an increased likelihood of having reduced susceptibility to treatment with lopinavir, comprising:
   (a) detecting, in said HIV, the presence or absence of one or more of the HIV protease mutations listed in Table 7;
   (b) assigning a weighting factor to each mutation as provided in Table 7; and
   (c) adding said weighting factors to get a total score for said HIV,
wherein said HIV has an increased likelihood of being resistant to treatment with lopinavir if said total score is equal to or greater than 6.

2. The method of claim 1, wherein said HIV has an increased likelihood of being resistant to treatment with lopinavir if said total score is equal to or greater than 7.

3. The method of claim 1, wherein said HIV has an increased likelihood of being resistant to treatment with lopinavir if said total score is equal to or greater than 8.

4. The method of claim 1, wherein the mutation is detected in a nucleic acid of said HIV that encodes the protease.

5. The method of claim 4, wherein said presence or absence of said mutation in said protease is detected by hybridization with a sequence-specific oligonucleotide probe to a nucleic acid sequence of said human immunodeficiency virus encoding said mutation, wherein the occurrence of hybridization indicates said presence or absence of said mutation.

6. The method of claim 5 wherein said sequence-specific oligonucleotide probe hybridizes to a nucleic acid encoding said mutation and the presence of hybridization indicates the presence of said mutation.

7. The method of claim 4, wherein said presence or absence of said mutation in said protease is detected by nucleic acid sequencing.

8. The method of claim 1, wherein said human immunodeficiency virus is human immunodeficiency virus type 1 (HIV-1).

9. The method of claim 1 wherein the method comprises detecting the presence or absence of a mutation associated with reduced susceptibility to treatment with lopinavir at 2 or more of the amino acid positions.

10. A method for determining whether an individual infected with a human immunodeficiency virus (HIV) has an increased likelihood of having reduced susceptibility to treatment with lopinavir, comprising:
   (a) detecting, in a sample from said individual, the presence or absence of one or more of the HIV protease mutations listed in Table 7;
   (b) assigning a weighting factor to each mutation as provided in Table 7; and
   (c) adding said weighting factors to get a total score for said individual wherein said individual has an increased likelihood of being resistant to treatment with lopinavir if said total score is equal to or greater than 6.

11. The method of claim 10, wherein said individual has an increased likelihood of being resistant to treatment with lopinavir if said total score is equal to or greater than 7.

12. The method of claim 10, wherein said individual has an increased likelihood of being resistant to treatment with lopinavir if said total score is equal to or greater than 8.

13. The method of claim 10, wherein the mutation is detected in a nucleic acid of said HIV that encodes the protease.

14. The method of claim 13, wherein said presence or absence of said mutation in said protease is detected by hybridization with a sequence-specific oligonucleotide probe to a nucleic acid sequence of said human immunodeficiency virus encoding said mutation, wherein the occurrence of hybridization indicates said presence or absence of said mutation.

15. The method of claim 14 wherein said sequence-specific oligonucleotide probe hybridizes to a nucleic acid encoding said mutation and the presence of hybridization indicates the presence of said mutation.

16. The method of claim 13, wherein said presence or absence of said mutation in said protease is detected by nucleic acid sequencing.

17. The method of claim 10, wherein said human immunodeficiency virus is human immunodeficiency virus type 1 (HIV-1).

18. The method of claim 10 wherein the method comprises detecting the presence or absence of a mutation associated with reduced susceptibility to treatment with lopinavir at 2 or more of the amino acid positions.

19. The method of claim 10, wherein the individual is undergoing or has undergone prior treatment with lopinavir or a different protease inhibitor.

* * * * *

SEQUENCE LISTING

<160> NUMBER OF SEQ ID NOS: 2

<210> SEQ ID NO 1
<211> LENGTH: 99
<212> TYPE: PRT
<213> ORGANISM: Human immunodeficiency virus

<400> SEQUENCE: 1

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60
```

-continued

```
Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 2
<211> LENGTH: 297
<212> TYPE: DNA
<213> ORGANISM: Human immunodeficiency virus

<400> SEQUENCE: 2
cctcagatca ctctttggca gcgacccctc gtcacaataa agatagggggg gcaattaaag      60 gaagctctat tagatacagg agcagatgat acagtattag aagaaatgaa tttgccagga     120
agatggaaac caaaaatgat agggggaatt ggaggtttta tcaaagtaag acagtatgat     180
cagatactca tagaaatctg cggacataaa gctataggta cagtattagt aggacctaca     240
cctgtcaaca taattggaag aaatctgttg actcagattg gctgcacttt aaatttt       297
```